(12) United States Patent
Kashani-Sabet et al.

(10) Patent No.: US 11,142,796 B2
(45) Date of Patent: Oct. 12, 2021

(54) MIR-18B FOR USE AS A MARKER OF CANCER PROGRESSION AND TARGET FOR THERAPIES TO TREAT CANCER

(71) Applicant: SUTTER WEST BAY HOSPITALS, San Francisco, CA (US)

(72) Inventors: Mohammed Kashani-Sabet, San Francisco, CA (US); Altaf A. Dar, San Bruno, CA (US)

(73) Assignee: Sutter Bay Hospitals, San Francisco, CA (US)

( * ) Notice: Subject to any disclaimer, the term of this patent is extended or adjusted under 35 U.S.C. 154(b) by 0 days.

(21) Appl. No.: 14/429,211

(22) PCT Filed: Sep. 19, 2013

(86) PCT No.: PCT/US2013/060589
§ 371 (c)(1),
(2) Date: Mar. 18, 2015

(87) PCT Pub. No.: WO2014/047267
PCT Pub. Date: Mar. 27, 2014

(65) Prior Publication Data
US 2015/0211071 A1    Jul. 30, 2015

Related U.S. Application Data

(60) Provisional application No. 61/703,057, filed on Sep. 19, 2012.

(51) Int. Cl.
| | |
|---|---|
| *C12Q 1/6886* | (2018.01) |
| *G01N 33/574* | (2006.01) |
| *C12N 15/113* | (2010.01) |
| *A61K 31/7088* | (2006.01) |
| *A61K 45/06* | (2006.01) |
| *C12N 15/52* | (2006.01) |

(52) U.S. Cl.
CPC ........ *C12Q 1/6886* (2013.01); *A61K 31/7088* (2013.01); *A61K 45/06* (2013.01); *C12N 15/113* (2013.01); *C12N 15/52* (2013.01); *G01N 33/5743* (2013.01); *C12N 2310/141* (2013.01); *C12Q 2600/112* (2013.01); *C12Q 2600/154* (2013.01); *C12Q 2600/178* (2013.01); *G01N 2800/56* (2013.01)

(58) Field of Classification Search
None
See application file for complete search history.

(56) References Cited

FOREIGN PATENT DOCUMENTS

WO    2012005572 A1    1/2012

OTHER PUBLICATIONS

Pavicic et al ( Mol Med (2011) vol. 17, pp. 726-735).*
Ehrlich et al. (2002 Oncogene vol. 21 p. 5400).*
Cottrell (Clinical Biochemistry 2004 vol. 37 p. 595).*
Walsh et al teaches (Genes & Development (1999) vol. 13, pp. 26-36).*
Brooks et al ( Cancers Causes control (2009) vol. 20, pp. 1539-1550).*
Murakami et al (BMC cancer (2013) vol. 13:99).*
Liang ( BMC genomics (2007) vol. 8, 199, pp. 1-20).*
Cheung et al (Nature Genetics, 2003, vol. 33, pp. 422-425).*
Berks (cellular Oncology (2004) vol. 26, pp. 291-299).*
Lujambio et al (Proceedings National Academy of Sciences (2008) vol. 106, pp. 13556-13561).*
Haqq et al (Proceedings National Academy of Sciences (2005) vol. 102, pp. 6092-6097).*
Dar (Journal national Cancer institute (2013, vol. 105, pp. 433-442 and supplemental info) (published online Jan. 30, 2013).*
Yoshimoto (Breast Cancer Res Treat (2011) vol. 130, pp. 331-339).*
Li (bioinformatics (2002) vol. 18, pp. 1427-1431).*
Gen Bank accession NC_000023.10 (https://www.ncbi.nlm.nih.gov/nuccore/224589822?sat=14&satkey=8929811, Oct. 25, 2010).*
Eades (The Journal of Biological Chemistry (2011) vol. 286, pp. 25992-26002).*
Howell (The Ochsner Journal (2010) vol. 10, pp. 83-92).*
Hauschild, Axel et al., "Dabrafenib in BRAF-mutated metastatic melanoma: a multicentre, open-label, phase 3 randomised controlled trial", The Lancet, vol. 380, No. 9839, Jul. 28, 2012, pp. 358-365.
Caramuta et al., "MicroRNA expression profiles associated with mutational status and survival in malignant melanoma," J. of Invest. Dermatol., 130(8):2062-2070, 2010.
Dar et al., "Abstract LB-470: Tumor suppressor role of microRNA 18b in melanoma," Cancer Research, vol. 72, No. 8, Suppl. 1, Proceedings of the 103rd Annual Meeting of the AACR, Apr. 15, 2012.
Dar et al., "The role fo miR-18b in MDM2-p53 pathway signaling and melanoma progression," J. of the Natl. Cancer Institute, 105(6):433-442, Jan. 2013.
Kim, Seung Beom, International Search Report and Written Opinion, PCT/US2013/060589, Korean Intellectual Property Office, Dec. 3, 2013.
Xu et al., "Differential expression of microRNAs during melanoma progression: miR-200c, MiR-205 and MiR-211 are downregulated in melanoma and act as tumour suppressors," Br. J. of Cancer, 106(3): 553-561, Jan. 2012.
Yoshimoto et al., "Distinct expression of microRNAs that directly target estrogen receptor alpha in human breast cancer," Breast Cancer Res. and Treatment, 130(1):331-339, 2011.

* cited by examiner

*Primary Examiner* — Steven Pohnert
(74) *Attorney, Agent, or Firm* — Gavrilovich, Dodd & Lindsey LLP

(57) ABSTRACT

The disclosure provides methods for predicting and/or determining whether a subject has cancer based on the level of expression of miR-18b. The disclosure also provides methods for determining whether a cancer in a subject is progressing or regressing based upon the change of expression levels of miR-18b between two time points. The disclosure further provides methods to treat a subject with a cancer by administering a polynucleotide comprising miR-18b and/or an agent that enhances the expression of miR-18b.

3 Claims, 19 Drawing Sheets

Specification includes a Sequence Listing.

MIR-18B FOR USE AS A MARKER OF CANCER PROGRESSION AND TARGET FOR THERAPIES TO TREAT CANCER

CROSS REFERENCE TO RELATED APPLICATIONS

This application is a U.S. National Stage Application filed under 35 U.S.C. § 371 and claims priority to International Application No. PCT/US2013/060589, filed Sep. 19, 2013, which application claims priority under 35 U.S.C. § 119 from Provisional Application Ser. No. 61/703,057, filed Sep. 19, 2012, the disclosures of which are incorporated herein by reference.

GOVERNMENT LICENSE RIGHTS

This invention was made with Government support under Grant Nos. CA114337 and CA122947, awarded by the National Institutes of Health/National Cancer Institute. The Government has certain rights in this invention.

TECHNICAL FIELD

The disclosure provides methods for cancer diagnosis, subject survival rate, and/or cancer progression based upon measuring the expression levels of microRNA, miR-18b. The disclosure further provides a method for treating a subject with cancer by enhancing the expression of miR-18b.

BACKGROUND

Melanoma, a life threatening malignancy with a poor prognosis in its advanced stages, accounts for 80% of skin cancer deaths. It is the sixth most common cancer in the US, accounting for more than 60,000 new cases each year. Melanomas are unique among solid tumors in that they rarely harbor mutations in the p53 gene. The mechanism by which the p53 pathway is suppressed in many melanomas is unclear, beyond mutations in the CKDN2A gene, which can result in p14ARF loss. Beyond surgical removal of the primary tumor, there is currently no curative standard therapy available, especially for more advanced stages. Accordingly, there has been a long felt need in the industry of developing molecular markers that can be used to not only track melanoma progression but also could be used as targets for regulating and suppressing melanoma progression.

SUMMARY

The disclosure provides a functional role for miR-18b in cancer, the molecular mechanism regulating its expression, and identifies the proto-oncogene MDM2 as a target of miR-18b action in cancer.

The disclosure provides a method of prognosticating as to whether a subject has a cancer, such as melanoma, comprising: (i) obtaining a biological sample, such as a tissue biopsy, from a subject; (ii) measuring the expression level of pre-miR-18b (UGUGU*UAAGGUGC AUCUAGUG CAGUUAG* UGAAGCAGCUUAGAAUCUAC *UGCCCUAA AUGCCCCU UC UGGC* A; SEQ ID NO:2), or processed/mature miR-18b-5p (UAAGGUG-CAUCUAGUGCAGUUAG; SEQ ID NO:1 (6-28 of SEQ ID NO:2); or -miR-18b-3p UGCCCUAAAUGCCCC-UUCUGGC; SEQ ID NO:3 (49-70 of SEQ ID NO:2)) in the subject's biological sample; (iii) comparing the expression level of miR-18b in the subject's biological sample with the expression level of miR-18b from one or more control biological samples, such as from tissue biopsies of benign nevi; and (iv) prognosticating whether the subject has cancer based on having a lower expression level for miR-18b in comparison to the mean expression level of miR-18b in the control samples. In another embodiment, the control biological samples or benign nevi are from the same subject or alternatively not from the same subject.

The disclosure provides a method of determining whether a subject has a cancer, comprising: (i) obtaining a biological sample, such as a tissue biopsy, from a subject; (ii) measuring the expression level of miR-18b in the subject's biological sample; (iii) comparing the expression level of miR-18b in the subject's biological sample with the mean expression level of miR-18b from one or more control biological samples, such as from tissue biopsies of benign nevi; and (iv) determining whether the subject has cancer based on having a significantly lower expression level for miR-18b in comparison to the expression levels for miR-18b in the control samples. In another embodiment, the control biological samples are from the same subject or alternatively from a different subject.

The disclosure provides a method of determining whether a cancer, such as a melanoma, in a subject is progressing or in recovery, comprising: (i) obtaining a biological sample, such as a tissue biopsy, from a subject at a first time point; (ii) measuring the expression level of miR-18b in the subject's biological sample from the first time point; (iii) obtaining a biological sample, such as a tissue biopsy, from a subject at a second time point; (iv) measuring the expression level of miR-18b in the subject's biological sample from the second time point; (v) comparing the expression levels of miR-18b from the first time point with the expression levels from the second time point; and (vi) determining whether a cancer is progressing or is in recovery based upon the change in expression levels of miR-18b from the two time points, wherein an increase in miR-18b expression levels between the first time point and the second time point indicates that the cancer is in recovery, and wherein a decrease in miR-18b expression levels between the first time point and the second time point indicates the cancer is progressing.

The disclosure provides a method of prognosticating the survival rate of a subject who has a cancer, such as a melanoma, comprising: (i) obtaining a biological sample from a subject at a first time point; (ii) measuring the expression level of miR-18b in the subject's biological sample from the first time point; (iii) obtaining a biological sample from a subject at a second time point; (iv) measuring the expression level of miR-18b in the subject's biological sample, such as tissue biopsy, from the second time point; (v) comparing the expression levels of miR-18b from the first time point with the expression levels from the second time point; and (vi) prognosticating a subject's survival rate based upon the change in expression levels of miR-18b from the two time points, wherein an increase in miR-18b expression levels between the first time point and the second time point indicates a better survival rate for the subject, and wherein a decrease in the miR-18b expression levels between the first time point and the second time point indicates a poorer survival rate for the subject.

The disclosure provides a method of treating a cancer, such as a melanoma, in a subject, the method comprising: administering an effective amount of an agent that enhances the expression of miR-18b. In one embodiment, the disclosure provides a methods wherein the agent that enhances the expression of miR-18b is a vector that expresses miR-18b comprising SEQ ID NO:1 or a sequence that is at least 98% identical to SEQ ID NO:1. In one embodiment, the vector is a replication competent retroviral vector such as an MLV (see e.g., International Publication No. WO 2010/036986, the disclosure of which is incorporated herein) or adenoviral vector. In other embodiments, the vector may be a replication defective vector. In yet other embodiment, a delivery system comprising double stranded RNA binding domains and protein transduction domains (see, e.g., U.S. Pat. Publ. No. 20090093026-A1, the disclosure of which is incorporated herein by reference) or nanoparticle that can neutralize the anionic charge of the miR-18b can be used. In yet a further embodiment, the enhancing of the expression of miR-18b results in inhibiting or preventing the proliferation of cancerous cells. In another embodiment, the enhancing of the expression of miR-18b results in a decrease in the expression of MDM2 in cancerous cells. In yet another embodiment, an additional therapeutic agent is administered in conjunction with a polynucleotide comprising miR-18b and/or an agent that enhances the expression of miR-18b. Examples of additional therapeutic agents include but are not limited to, platinum analogs, alkylating agents, alkyl sulfonates, androgens, anti-adrenals, anti-androgens, antibiotics, anti-estrogens, aromatase inhibiting 4(5)-imidazoles, anti-metabolites, folic acid analogues, ethylenimines and methylamelamines, folic acid replenishers, nitrogen mustards, nitrosureas, purine analogs, pyrimidine analogs, topoisomerase inhibitors, thymidylate synthase inhibitors, anti-cancer antibodies, chemotherapeutics, targeted therapies such as vemurafenib, dabrafenib, trametinib, erlotinib and Gleevec and de-methylation agents. In a particular embodiment, the additional therapeutic agent is cisplatin.

The disclosure provides for one or more embodiments set forth in the accompanying drawings and the description below. Other features, objects, and advantages of the invention will be apparent from the description and drawings, and from the claims.

DETAILED DESCRIPTION

Figure 1A:
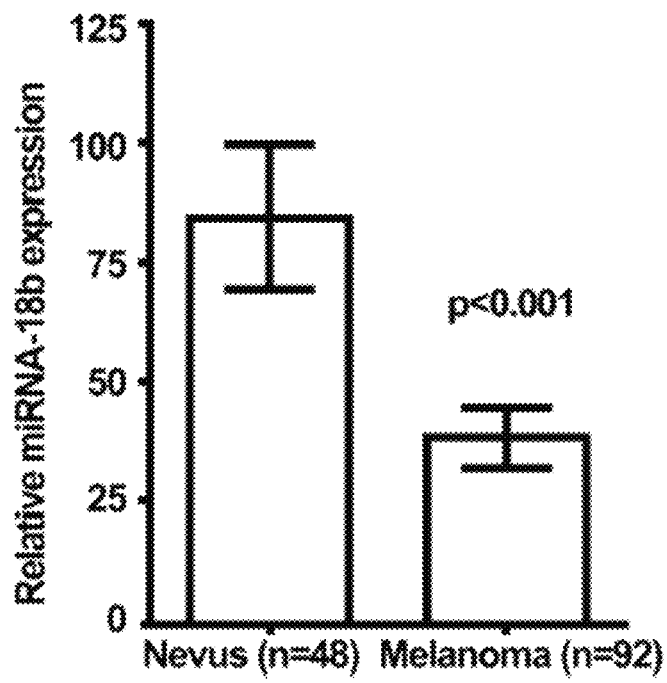
FIG. 1A-C shows miR-18b expression is suppressed in melanoma. (A) miRNA-quantitative analysis showing significant suppression in miR-18b expression in a cohort of melanoma samples as compared to nevus samples. (B) Suppression in miR-18b in melanoma samples predicts overall survival. Low miR-18b expressors were defined as samples with miR-18b expression below the mean, and high miR-18b expressors were defined as samples with miR-18b expression above the mean. (C) miR-18b expression is suppressed in melanoma cell lines as compared to normal human melanocytes. Wherein, * is p<0.05.

As used herein and in the appended claims, the singular forms "a," "an," and "the" include plural referents unless the context clearly dictates otherwise. Thus, for example, reference to "a probe" includes a plurality of such cells and reference to "the cell" includes reference to one or more cells and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Melanoma cells are highly resistant to chemotherapy, resulting in low response rates to the administering of chemotherapeutic reagents (La Porta Calif., *Curr Cancer Drug Targets* 9:391-7 (2009)). In addition, melanoma cells are common and represent a major cause of skin disease and surgery.

MicroRNAs (miRNAs) have emerged as a novel class of potential cancer biomarker or target for therapy. miRNAs are non-protein-coding sequences thought to regulate >90% of human genes (Miranda et al., *Cell* 126:1203-17 (2006)). Deregulation of miRNA expression has been identified in a number of cancers and accumulating data indicates that some miRNAs can function as oncogenes or tumor suppressor genes (Volinia et al. *Proc Natl Acad Sci USA* 103:2257-61 (2006); Porkka et al., *Cancer Res* 67:6130-5 (2007)).

miRNAs are expressed in a tissue-specific manner and can play important roles in cell proliferation, apoptosis, and differentiation (Sempere et al., *Genome Biol* 5:R13 (2004); and Bartel D P. *Cell* 116:281-97 (2004)). Inactivation of oncogenic miRNAs or restoration of tumor-suppressor miRNAs may have great potential for cancer treatment (Medina et al., *Nature* 467:86-90; Obad et al. *Nat Genet.* 43: 371-8; Saito et al., *Cancer Cell* 9: 435-43 (2006); Lujambio et al. *Cancer Res* 67:1424-9 (2007); and Lujambio et al. *Proc Natl Acad Sci USA* 105:13556-61 (2008)). In addition, miRNAs are being assessed as possible biomarkers to aid in the diagnosis and prognosis of different cancers, including melanoma (Yi et al., *Cell Death Differ* 17:229-35 (2010); and Bartels et al., *Clin Chem* 55:623-31 (2009)). To date, few miRNA expression profiling analyses have been performed on human melanoma samples, and some candidate miRNAs have emerged with putative roles in melanoma progression (Mueller et al., *Br J Cancer* 101:551-6 (2009); Bemis et al. *Cancer Res* 68: 1362-8 (2008); Felicetti et al. *Cancer Res* 68: 2745-54 (2008); Segura et al., *Proc Natl Acad Sci USA* 106:1814-9 (2009); and Dar et al., *J Biol Chem* 286: 16606-14 (2011)).

Recently, tumor-suppressive miRNAs have shown to be inactivated by DNA hypermethylation of CpG sites (Chuang et al., *Pediatr Res* 61:24R-9R (2007)). The DNA methylation profile of tumors has been used to define tumor type, clinical prognosis and response to therapy (Esteller M., *N Engl J Med* 358:1148-59 (2008); Rodriguez-Paredes et al., *Nat Med* 17:330-9). Epigenetic silencing of miRNAs can be involved in acquisition of the invasive and metastatic phenotype (Lujambio et al., *Cell Cycle* 8:377-82 (2009)). Despite the accumulating evidence regarding the role of various of miRNAs in cancer, very limited information is available about the repertoire and function of miRNAs in melanoma, and few targets of miRNAs in melanoma have been identified. A handful of studies have assessed the levels of various miRNAs through microarray expression profiling or have studied the mechanisms of action of selected miRNAs in this tumor type (Gaur et al., *Cancer Res* 67: 2456-68 (2007); Philippidou et al., *Cancer Res* (2010); and Segura et al., *Proc Natl Acad Sci USA* 106: 1814-9 (2009)). For example, miR-221 and miR-222 have been implicated in melanoma progression through the regulation of p27 expression (Felicetti et al., *Cancer Res* 68:2745-54 (2008)). Aberrant expression of miR-182 promotes melanoma metastasis by repressing FOXO3 and microphthalmia-associated transcription factor Segura et al., *Proc Natl Acad Sci USA* 106: 1814-9 (2009)). miR-532-3p has been shown to regulate RUNX3 in cutaneous melanoma (Kitago et al., *Clin Cancer Res* 15:2988-94 (2009)); miR-193 to regulate Mcl-1 (Chen et al., *Am J Pathol* 179: 2162-8 (2011)); and miRNA-137 to target MITF (Bemis et al., *Cancer Res* 68: 1362-8 (2008)) in melanoma. A role for miR-205 in suppression of melanoma growth and in induction of senescence was reported (Dar et al., *J Biol Chem* 286: 16606-14 (2011)).

miR-18b has been reported to be differentially expressed in certain cancers using microarray screens, but a functional role in tumorigenesis is lacking, and its targets of action are yet to be determined (Kim et al., *Histopathology* 57:734-43 (2010)). The disclosure provides for the characterization of miR-18b including identifying a mechanism by which its expression is silenced, and demonstrating its functional role as a tumor suppressor in melanoma. In the studies presented herein, miR-18b was found to be downregulated in melanomas in comparison to nevi, and in melanoma cell lines in comparison to normal melanocytes. In a particular embodiment, by measuring the level of miR-18b expression in cancerous cells from a subject, one could predict the survival rate of the subject, such that a lower miR-18b expression level is correlative to a lower survival rate of the subject.

The disclosure provides that DNA methylation is an important molecular mechanism that is responsible for suppression of miR-18b expression in melanoma. This disclosure adds to the growing body of evidence demonstrating the role of DNA methylation-mediated downregulation of miRNAs by proximal CpG islands (Saito et al., Cancer Cell 9:435-43 (2006); Kozaki et al., Cancer Res 68:2094-105 (2008); Iorio et al., Biochim Biophys Acta 1799:694-701; and Toyota et al., Cancer Res 68:4123-32 (2008)). Aberrant DNA methylation and histone modifications work in concert to silence many tumor suppressor genes in human cancers (Nakagawa et al., J Urol 173: 1767-71 (2005); and Kristeleit et al., Expert Opin Emerg Drugs 9: 135-54 (2004)). Furthermore, hyper-acetylation of histone lysine residues facilitates transcriptional activation and induction of gene expression (Kristeleit et al., Expert Opin Emerg Drugs 9: 135-54 (2004); and Archer et al., Curr Opin Genet Dev 9: 171-4 (1999)). The studies provided herein indicate that miR-18b overexpression in melanoma cell lines results in the increased enrichment of acetyl H3, acetyl H4, 2H3K4, which is indicative of active gene expression, whereas repressive chromatin modifications (2H3K9 and 3H3K4) were suppressed. Additional studies provided herein establish that miR-18b has distinct CpG islands in its upstream region which are hypermethylated, leading to its silencing through tumor-specific DNA hypermethylation.

A significant obstacle to understanding miRNA function has been the relative paucity of experimentally validated targets. To determine the effectors of miR-18b, in-silico algorithms and functional analyses identified MDM2 as a target. The results presented herein indicate an inverse correlation between expression of miR-18b and that of MDM2 in a panel of melanoma cell lines. miR-18b was found to directly target the 3'UTR of MDM2. In addition, a significant downregulation of MDM2 protein levels was observed after miR-18b overexpression, indicating the post-transcriptional regulation of MDM2 via targeting its 3'UTR. MDM2 has been shown to be overexpressed in melanoma progression (Polsky et al., J Natl Cancer Inst 94: 1803-6 (2002)), and likely induces cellular transformation through its association with p53 (to promote p53 degradation) and through its ability to stimulate the E2F1/DP1 transcription complex. Furthermore, the studies presented herein demonstrate that MDM2 downregulation following miR-18b overexpression was accompanied by activation of p53.

p53 has potent tumor suppressor activity and is inactivated in most tumors through point mutations. Melanoma is relatively unique in human solid tumors in that p53 mutations have been rarely described (Sparrow et al., Melanoma Res 5: 93-100 (1995)). p53 can also be inactivated through overexpression of MDM2 or loss or inactivation of $p14^{ARF}$ and $p16^{INK4a}$ (Toledo et al., Nat Rev Cancer 6:909-23 (2006)). $p14^{ARF}$ expression was unchanged following miR-18b overexpression, emphasizing the direct role played by miR-18b to suppress MDM2 and activate p53. The results provided herein, indicate in the first instance of its kind that the loss of miR-18b (through hypermethylation) is an important alternative mechanism to effect suppression of p53 and the p53 pathway in melanoma cells. Reactivation of p53 function has been actively pursued as a therapeutic approach in cancer (Martins et al., Cell 127: 1323-34 (2006)). Thus, in one embodiment, the disclosure provides methods and compositions for expressing or increasing expression of p53 in cancerous cells by overexpressing miR-18b. For example, in one embodiment, as described above, hypermethylation reduces miR-18b, accordingly agents the inhibit methylation can be used to increase miR-18b expression and thus p53 expression. In a certain embodiment, a subject with melanoma can be treated by administering a de-methylating agent so as to counteract, impede, inhibit or suppress tumor-specific DNA hypermethylation of miR-18b in melanoma cells. Examples of de-methylating agents include, but are not limited to, cytidine derivatives, including 5-azacytidine and 5-azadeoxycytidine; and procainamide and derivatives, such as procaine.

Furthermore, the disclosure demonstrates that miR-18b overexpression results in the upregulation of PUMA, a pro-apoptotic protein, as well as the cell cycle regulator p21, and suppresses expression of the anti-apoptotic proteins BCL-2 and BCL-XL. These changes in gene expression were accompanied by significant inhibition of cell proliferation, colony formation and induction of apoptosis in melanoma cells, an observation that was confirmed in two different human melanoma cell lines. These effects were further confirmed following stable overexpression of miR-18b in 1205-Lu cells. In addition, in vivo studies provided herein demonstrate a striking reduction in subcutaneous tumor cell growth in mice following miR-18b overexpression. These findings identify miR-18b as a novel tumor suppressor in melanoma. In a certain embodiment, p53 and the apoptotic cascade can be activated by overexpressing miR-18b. The studies disclosed herein, demonstrate that miR-18b overexpression significantly suppresses the migratory and invasive ability of melanoma cell lines.

In one embodiment, subjects with melanoma can be treated by enhancing the expression of miR-18b. In a further embodiment, subjects with cancer, such as melanoma, can be treated by enhancing the expression of miR-18b in conjugation with administering one or more additional therapeutic agents. Examples of therapeutic agents include but are not limited to, anticancer agents, de-methylating agents, alkylating agents, anti-metabolite agents, mitotic inhibitors, tyrosine kinase inhibitors, topoisomerase inhibitors, cancer immunotherapy monoclonal antibodies, anti-tumor antibiotic agents, and targeted anti-cancer agents. In a particular embodiment, subjects with cancer, such as melanoma, can be treated by enhancing the expression of miR-18b in combination with the administration of cisplatin. In another embodiment, subjects with cancer, such as melanoma, can be treated by enhancing the expression of miR-18b in combination with the administration of a BRAF inhibitor such as, for example, dabrafenib. As used herein, "BRAF inhibitors" refers to drugs that target an acquired mutation of B-RAF that is associated with cancer, such as .sup.V600EB-RAF. Representative examples of such a B-RAF inhibitor include PLX4032/vemurafenib or other similar agents, such as GSK2118436/dabrafenib Epithelial-to-mesenchymal transition (EMT) has been shown to play a major role in invasion and metastasis of epithelial tumors as well as melanoma (Alonso et al., Cancer Res 67:3450-60 (2007)). Epithelial-to-mesenchymal regulators (EMTRs) such as Snail, Slug, and Twist are crucial to this process, which is primarily coordinated by the disappearance or loss of markers such as E-cadherin, and the concomitant activation of markers such as vimentin, fibronectin and N-cadherin. The studies presented herein, demonstrate that the overexpression of miR-18b results in suppression of vimentin, slug, and N-cadherin while restoring E-cadherin levels in melanoma cells. These results indicate that miR-18b can mediate EMT, representing one possible mechanism through which it affects melanoma migration and invasion. The studies disclosed herein, demonstrate that miR-18b overexpression significantly suppresses the migratory and invasive ability of melanoma cell lines.

In another embodiment, the disclosure provides a method of treating a cancer, the method comprising administering an effective amount of an agent that enhances the expression of miR-18b.

The terms "treat", "treating" and "treatment", as used herein, refer to ameliorating symptoms associated with a disease or condition, for example, a melanoma, including preventing or delaying the onset of the disease symptoms, and/or lessening the severity or frequency of symptoms of the disease or condition. The terms "subject" and "individual" are defined herein to include animals, such as mammals, including but not limited to, primates, cows, sheep, goats, horses, dogs, cats, rabbits, guinea pigs, rats, mice or other bovine, ovine, equine, canine, feline, rodent, or murine species. In a preferred embodiment, the mammal is a human.

As used herein, an "effective amount" of miR-18b is an amount sufficient to inhibit proliferation or invasiveness of a cancer cell in a subject suffering from a cancer. One skilled in the art can readily determine an effective amount of miR-18b gene product to be administered to a given subject, by taking into account factors, such as the size and weight of the subject; the extent of disease penetration; the age, health and sex of the subject; the route of administration; and whether the administration is regional or systemic.

Cancers that may be treated by compositions comprising polynucleotides comprising miR-18b and/or agents that increase miR-18b expression, include, tumors that are not vascularized, or not yet substantially vascularized, as well as vascularized tumors. The cancers may be comprised of non-solid tumors (such as leukemias and lymphomas) or may be solid tumors.

Types of cancers treated with the agent or composition of the disclosure include carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers alike may be treated in accordance with the methods disclosed herein.

Examples of tumors/cancers which may be treated include, ovarian, breast (including HER2+ and metastatic), colorectal, colon, renal, rectal, pancreatic, prostate, stomach, gastrointestinal, gastric, stomach, esophageal, bile duct, lung (including small cell and non-small cell lung tumors; adenocarcinoma of the lung and squamous carcinoma of the lung), liver, epidermoid tumors, squamous tumors such as head and neck tumors, epithelial squamous cell cancer, thyroid, cervical, neuroendocrine tumors of the digestive system, neuroendocrine tumors, cancer of the peritoneum, hepatocellular cancer, hepatoblastoma, HPCR, glioblastoma, bladder cancer, hepatoma, endometrial or uterine carcinoma, salivary gland carcinoma, kidney or renal cancer, bone cancer, soft tissue sarcoma (including embryonal and alveolar rhabdomyosarcoma, GIST, alveolar soft part sarcoma and clear cell sarcoma), cholangiocarcinoma, bile cancer, gallbladder carcinoma, myeloma, vulval cancer, hepatic carcinoma, anal carcinoma, penile carcinoma, retinal, hematopoietic cancer, androgen-dependent tumors, androgen-independent tumors, Other examples include Kaposi's sarcoma, synovial sarcoma, vasoactive intestinal peptide secreting tumor, CNS neoplasms, neuroblastomas, capillary hemangioblastomas, meningiomas, and cerebral metastases, melanoma, rhabdomyosarcoma, glioblastoma, including glioblastoma multiforme, EMB, RMS, ALV, medulloblastoma, ependymoma, Wilm's cancer, Ewing's cancer, osteosarcoma, PNT, rhabdoid, rhabdomyosarcoma, retinoblastoma, adrenal cortical cancer, adrenal cancer, and leiomyosarcoma. In a certain embodiment, the cancer to be treated is melanoma.

In a particular embodiment, the disclosure provides a method of treating cancer, such as melanoma, in a subject, the method comprising administering an effective amount of an agent that enhances the expression of miR-18b. In another embodiment, the agent is a shRNA from a polymerase II or III promoter. In another embodiment, the agent is a double-stranded miRNA mimic. miRNA mimic technology is well known in the art. See e.g., Wang, Z., 2009, miRNA mimic technology, In MicroRNA Interference Technologies, pages 93-100, Springer-Link Publications. In another embodiment, the agent is an oligonucleotide based pre-miR-18b drug.

Polynucleotide therapy featuring a polynucleotide encoding an miRNA, such as miR-18b, is another therapeutic approach for enhancing a transcript number or expression level of the miRNA in a subject. Expression vectors encoding miR-18b can be delivered to cells of a subject for the treatment or prevention of a cancer. The nucleic acid molecules are delivered to the cells of a subject in a form in which they can be taken up and are advantageously expressed so that therapeutically effective levels can be achieved. Expression vectors that are able to express miR-18b are commercially available from various vendors.

Methods for delivering polynucleotides comprising miR-18b and/or agents that increase miR-18b expression to the cell include using a delivery system, such as liposomes, polymers, microspheres, gene therapy vectors, and naked DNA vectors.

Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., *Human Gene Therapy* 8:423-430 (1997); Kido et al., *Current Eye Research* 15:833-844 (1996); Bloomer et al., *Journal of Virology* 71:6641-6649 (1997); Naldini et al., *Science* 272:263-267 (1996); and Miyoshi et al., *Proc. Natl. Acad. Sci. U.S.A.* 94:10319 (1997)). For example, a polynucleotide encoding miR-18b can be cloned into a retroviral vector and its expression can be driven from an endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, *Human Gene Therapy* 15-14, (1990); Friedman, *Science* 244:1275-1281 (1989); Eglitis et al., *BioTechniques* 6:608-614 (1988); Tolstoshev et al., *Current Opinion in Biotechnology* 1:55-61 (1990); Sharp, *The Lancet* 337:1277-1278 (1991); Cornetta et al., *Nucleic Acid Research and Molecular Biology* 36(31):1-322 (1987); Anderson, *Science* 226:401-409 (1984); Moen, *Blood Cells* 17:407-416 (1991); Miller et al., *Biotechnology* 7:980-990 (1989); Le Gal La Salle et al., *Science* 259:988-990 (1993); and Johnson, *Chest* 107:77 S-83S (1995)). Retroviral vectors are particularly well developed and have been used in clinical settings (Rosenberg et al., *N. Engl. J. Med* 323:370 (1990); Anderson et al., U.S. Pat. No. 5,399,346). Non-viral approaches can also be employed for the introduction of a miR-18b based therapeutic to a cell of a patient diagnosed as having a neoplasia. For example, a polynucleotide comprising miR-18b can be introduced into a cell by administering the nucleic acid in the presence of cationic lipid (Feigner et al., *Proc. Natl. Acad. Sci. U.S.A.* 84:7413 (1987); Ono et al., *Neuroscience Letters* 17:259 (1990); Brigham et al., *Am. J. Med. Sci.* 298:278 (1989); and Staubinger et al., *Methods in Enzymology* 101:512 (1983)); asialoorosoinucoid-polylysine conjugation (Wu et al. *Journal of Biological Chemistry* 263:14621 (1988); Wu et al., *Journal of Biological Chemistry* 264:16985 (1989); or by micro-injection under surgical conditions (Wolff et al., *Science* 247:1465 (1990). A polynucleotide comprising miR-18b and/or an agent that enhances miR-18b expression can be administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. miR-18b expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. For any particular subject, the specific dosage regimes should be adjusted over time according to the individual need and the professional judgment of the person administering or supervising the administration of the compositions.

In another embodiment, the disclosure provides therapeutic compositions comprising polynucleotides comprising miR-18b that increase the expression of miR-18b for the treatment of a cancer, such as melanoma. In another embodiment, the disclosure provides a pharmaceutical composition comprising an agent that enhances the expression of miR-18b. Examples of such agents include but are not limited to, compounds that prevent or suppress the methylation of miR-18b.

Polynucleotides comprising miR-18b and/or agents that increase the expression of miR-18b may be administered as part of a pharmaceutical composition. The pharmaceutical composition is preferably sterile and contains a therapeutically effective amount of a polynucleotide molecule comprising miR-18b and/or an agent that enhance the expression of miR-18b in a unit of weight or volume suitable for administration to a subject.

The therapeutic polynucleotide molecule comprising miR-18b and/or agents that increase the expression of miR-18b may be administered with a pharmaceutically-acceptable carrier, in unit dosage form. Conventional pharmaceutical practice may be employed to provide suitable formulations or compositions to administer the compounds to patients suffering from a cancer.

Carrier as used herein includes pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt forming counterions such as sodium; and/or nonionic surfactants such as TWEEN™, polyethylene glycol (PEG), and PLURONICS™.

Polynucleotides comprising miR-18b and/or agents that increase the expression of miR-18b may also be entrapped in microcapsules prepared, for example, by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nano-particles, and nanocapsules) or in macroemulsions. The formulations to be used for in vivo administration must be sterile. This is readily accomplished by filtration through sterile filtration membranes. Sustained-release preparations may be prepared. Suitable examples of sustained-release preparations include semipermeable matrices of solid hydrophobic polymers comprising a polynucleotide comprising miR-18b and/or an agent which enhances miR-18b expression, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release of molecules for shorter time periods.

In another embodiment, the pharmaceutical compositions comprising polynucleotides comprising miR-18b and/or agents that increase the expression of miR-18b are administered in conjunction with other therapeutic agents. "Conjunction" with respect to administering other therapeutic agents, refers to agents that may administered prior to, concurrently, or subsequent to pharmaceutical compositions comprising polynucleotides comprising miR-18b and/or agents which increase miR-18b expression.

In a particular embodiment, the pharmaceutical compositions comprising polynucleotides comprising miR-18b and/or agents that increase the expression of miR-18b are administered in conjunction with radiotherapy, chemotherapy, photodynamic therapy, surgery or other immunotherapy, to a patient who has a hyperproliferative disorder, such as cancer or a tumor. In one example, the pharmaceutical compositions of the disclosure are administered to a subject in conjunction with chemotherapy, radiation therapy, or both chemotherapy and radiation therapy. The pharmaceutical compositions of the disclosure may be administered in conjugation with one or more other prophylactic or therapeutic agents, including but not limited to cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, anti-cancer antibodies, or other therapeutic agents.

Examples of chemotherapeutic agents include, but are not limited to, platinum analogs such as cisplatin and carboplatin; vinblastine; platinum; proteins such as arginine deiminase and asparaginase; alkylating agents such as thiotepa and cyclophosphamide (CYTOXAN™), alkyl sulfonates such as busulfan, improsulfan and piposulfan; androgens such as calusterone, dromostanolone propionate, epitiostanol, mepitiostane, testolactone; anti-adrenals such as aminoglutethimide, mitotane, trilostane; anti-androgens such as flutamide, nilutamide, bicalutamide, leuprolide, and goserelin; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); anti-metabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; folic acid replenisher such as frolinic acid; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL™, Bristol-Myers Squibb Oncology, Princeton, N.J.) and docetaxel (TAXOTERE™, Rhne-Poulenc Rorer, Antony, France); topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylornithine (DMFO); elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofuran; spirogermanium; tenuazonic acid; triaziquone; 2,2',2''-trichlorotriethylamine; urethan; vindesine; dacarbazine; mannomustine; mitobronitol; mitolactol; pipobroman; gacyto sine; arabinoside ("Ara-C"), cyclophosphamide; thiotepa; chlorambucil; gemcitabine; 6-thioguanine; mercaptopurine; methotrexate; etoposide (VP-16); ifosfamide; mitomycin 0; mitoxantrone; vincristine; vinorelbine; navelbine; novantrone; teniposide; daunomycin; aminopterin; xeloda; ibandronate; CPT-11; retinoic acid; esperamicins; and capecitabine.

Administration of the pharmaceutical compositions disclosed herein may begin after the subject is determined to have a cancer or suspected of having a cancer. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

In addition to the therapeutic aspects of miR-18b expression and over expression, miR-18b can also be used as a diagnostic and prognostic marker of cancer treatment such as melanoma. In a certain embodiment, the expression level of miR-18b is determined from one or more biological samples from one or more subjects. The biological sample can be a tissue, blood, or other biological sample known to one of skill in the art. In one example, a tissue sample, such as a tissue biopsy, can be removed from a subject in accordance with a method known to one of skill in the art. In another example, a blood sample can be removed from a subject, and individual components of the blood sample can be isolated for extraction of nucleic acids or proteins by standard techniques.

In a particular embodiment, one or more control samples are obtained from one or more benign nevi from one or more subjects. Examples of nevi include, but are not limited to, compound nevus, spitz nevus, halo nevus, junctional nevus, pseudomelanoma, blue nevus, congenital melanocytic nevus, balloon cell nevus, dysplastic nevus/dysplastic nevus syndrome, acral nevus, Becker's nevus, Benign melanocytic nevus, and nevus spilus. The expression level of miR-18b in the control samples are measured, and in one embodiment, the mean expression level for miR-18b serves as the control expression level for miR-18b. In a particular embodiment, the one or more control samples and the test sample are obtained from the same subject. In an alternate embodiment, the one or more control samples are from multiple subjects, which may or may not include the test subject.

The expression level of miRNA can be quantitated and the level compared to control values. For example, the expression level of a miRNA in a test sample can be measured and the level determined. Thus, it can be determined if the level of miRNA is less than the expression level of the miRNA in a control sample (i.e., expression of the miRNA gene product is "under-expressed"). As used herein, the expression of an miRNA is "under-expressed" when the amount of miRNA expression in a test sample from a subject is less than the amount of the expression level of the miRNA in a control sample. In another embodiment, the expression level of an miRNA in a test sample can be greater than the expression level of the miRNA in a control sample (i.e., expression of the miR gene product is "over-expressed"). As used herein, the expression of an miRNA is "over-expressed" when the amount of miRNA expression in a test sample from a subject is greater than the amount of the expression level of the miRNA in a control sample. In yet another embodiment, the expression level of an miRNA in a test sample is equal to the expression level of the miRNA expression in a control sample.

The level of an miRNA in a sample can be measured by using any technique that is suitable for detecting RNA expression levels in a biological sample. Suitable techniques for determining RNA expression levels in cells from a biological sample are well known to those of skill in the art. Examples of such techniques include, but are not limited to, Northern blot analysis, RT-PCR, microarrays, in situ hybridization. In a particular embodiment, a high-throughput system, for example, a microarray, is used to measure the expression level of a plurality of genes.

In a certain embodiment, the level of an miRNA is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question.

Suitable probes for Northern blot hybridization of a given miRNA can be produced from the nucleic acid sequences of the miRNA. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11.

In one example, the nucleic acid probe can be labeled with, e.g., a radionucleotide, such as $^3$H, $^{32}$P, $^{33}$P, $^{14}$C, or $^{35}$S; a heavy metal; or a ligand capable of functioning as a specific binding pair member for a labeled ligand (e.g., biotin, avidin or an antibody), a fluorescent molecule, a chemiluminescent molecule, or an enzyme. Probes can be labeled to high specific activity by nick translation, random priming, or other methods known to one of skill in the art. For example, by replacing preexisting nucleotides with highly radioactive nucleotides according to the nick translation method, it is known to prepare $^{32}$P-labeled nucleic acid probes with a specific activity well in excess of $10^8$ cpm/microgram.

Autoradiographic detection of hybridization can then be performed by exposing hybridized filters to photographic film. Densitometric scanning of the photographic films exposed by the hybridized filters provides an accurate measurement of miRNA transcript levels. In another embodiment, miRNA gene transcript levels can be quantified by computerized imaging systems, such the Molecular Dynamics 400-B 2D Phosphorimager available from Amersham Biosciences, Piscataway, N.J.

In another embodiment, the random-primer method can be used to incorporate an analogue, for example, the dTTP analogue 5-(N-(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In a further embodiment, determining the levels of an miRNA expression can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the disclosure of which is incorporated herein by reference.

The relative number of miRNA gene transcripts in cells can also be determined by reverse transcription of miRNA gene transcripts, followed by amplification of the reverse-transcribed transcripts by polymerase chain reaction (RT-PCR). The levels of miRNA gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). The methods for quantitative RT-PCR and variations thereof are within the skill in the art. In another embodiment, a high throughput stem loop real-time quantitative polymerase chain reaction (RT-qPCR) is used to detect miRNA expression. See Mestdagh et al., *Nucleic Acid Research* 36(21) (2008)).

In some instances, it may be desirable to simultaneously determine the expression level of a plurality of different miRNA gene products in a sample. In other instances, it may be desirable to determine the expression level of the transcripts of all known miRNAs correlated with a cancer. In one embodiment, assessing cancer-specific expression levels for hundreds of miRNAs requires a large amount of total RNA (e.g., 20 µg for each Northern blot) and autoradiographic techniques that require radioactive isotopes. In another embodiment, an oligolibrary, in microchip format (i.e., a microarray), may be constructed containing a set of probe oligodeoxynucleotides that are specific for a set of miRNA genes. Using such a microarray, the expression level of multiple miRNAs in a biological sample can be determined by reverse transcribing the RNAs to generate a set of target oligodeoxynucleotides, and hybridizing them to probe oligodeoxynucleotides on the microarray to generate a hybridization, or expression, profile. The hybridization profile of the test sample can then be compared to the predetermined expression level of a control sample to determine which miRNAs have an altered expression level in cancer cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miRNA-specific probe oligonucleotide" or "probe oligonucleotide specific for an miRNA" is meant a probe oligonucleotide that has a sequence selected to hybridize to a specific miRNA gene product, or to a reverse transcript of the specific miRNA gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from a cancer tissue, and within a cancer tissue, different prognosis states (good or poor long term survival prospects, for example) may be determined.

By comparing expression profiles of a cancer tissue in different states, information regarding which genes are important (including both up- and down-regulation of genes) in each of these states, is obtained. The identification of sequences that are differentially expressed in a cancer tissue or normal tissue, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular patient). Similarly, diagnosis may be done or confirmed by comparing patient samples with the known expression profiles. Furthermore, these gene expression profiles (or individual genes) allow screening of drug candidates that suppress the cancer expression profile or convert a poor prognosis profile to a better prognosis profile.

The microarray can be prepared from gene-specific oligonucleotide probes generated from known miRNA sequences, including miR-18b. In one embodiment, the array contains two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length are 5'-amine modified at position C6 and printed using commercially available microarray systems, e.g., the GENEMACHINE, OMNIGRID 100 MICROARRAYER and AMERSHAM CODELINK activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRNA, in the patient sample. According to one embodiment, the labeled cDNA oligomer is a biotin-labeled cDNA, prepared from a biotin-labeled primer. The microarray is then processed by direct detection of the biotin-containing transcripts using, e.g., STREPTAVIDIN-ALEXA647 conjugate, and scanned utilizing conventional scanning methods. Image intensities of each spot on the array are proportional to the abundance of the corresponding miRNA in the patient sample.

In addition to use for quantitative expression level assays of a specific miRNA, a microchip containing miRNA-specific probe oligonucleotides corresponding to a substantial portion of the miRNome, preferably the entire miRNome, may be employed to carry out miRNA gene expression profiling, for analysis of miRNA expression patterns. Distinct miRNA signatures can be associated with established disease markers, or directly with a disease state.

According to the expression profiling methods described herein, total RNA from a sample from a subject suspected of having a cancer (e.g., melanoma) is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a control sample. An alteration in the signal is indicative of a chemotherapy response in the subject.

Other techniques for measuring miRNA gene expression are also within the skill in the art, and include various techniques for measuring rates of RNA transcription and degradation, including Rnase Protection Assays, Nuclear run-ons, slot blotting, etc.

In another embodiment, the disclosure provides a method for prognosticating the presence of a cancer in a subject. The method comprises the step of determining whether or not miR-18b is over-expressed or under-expressed in a biological sample from the subject, relative to the expression of miR-18b from one or more control samples. In a particular embodiment, the level of under-expression of miR-18b from a subject's biological sample in comparison to a control biological sample indicates whether the subject's sample is malignant. In a further embodiment, said malignancy is melanoma.

In yet another embodiment, the disclosure provides a method of determining the progression of cancer in a subject. The method comprises the step of measuring the expression level of miR-18b from biological samples taken from patient having a cancer at various time points, such that the change in the expression level of miR-18b between samples from the different time points indicates the progression or recovery from the cancer in the subject. In a particular embodiment, if the level of under-expression of miR-18b is increasing between earlier and later time points (i.e., the level of miR-18b is further decreasing or remaining the same) indicates that the subject's cancer is progressing to later stages. In an alternate embodiment, if the level of under-expression of miR-18b is decreasing (i.e., the level of miR-18b is increasing) between earlier and later timepoints indicates that the subject's cancer is in the process of recovering. In a further embodiment, said cancer is melanoma.

In yet another embodiment, the disclosure provides a method of determining the survival rate of a subject with cancer. The method comprises the step of measuring the expression level of miR-18b from biological samples taken from patient having a cancer at various time points, such that the change in the expression level of miR-18b between samples from the different time points indicates a decreased or increased survival rate of the subject. In a particular embodiment, if the level of under-expression of miR-18b is increasing between earlier and later timepoints would indicate that the subject's survival rate is decreasing. In an alternate embodiment, if the level of under-expression of miR-18b is decreasing between earlier and later timepoints would indicate that the subject's survival rate is improving. In a further embodiment, said cancer is melanoma.

In another embodiment, the disclosure provides a kit for determining a subject likelihood of having cancer and/or progression of cancer, said kit comprising: a) an oligonucleotide complementary to miR-18b; and b) optionally, reagents for the formation of the hybridization between said oligonucleotide and miR-18b. In another embodiment, the kit optionally includes directions for monitoring the nucleic acid molecule levels of a marker in a biological sample derived from a subject. In another embodiment, the kit comprises a sterile container which contains the primer, probe, or other detection regents; such containers can be boxes, ampoules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the primers or probes described herein and their use in diagnosing a cancer. Preferably, the kit further comprises any one or more of the reagents described in the diagnostic assays described herein. In other embodiments, the instructions include at least one of the following: description of the primer or probe; methods for using the enclosed materials for the diagnosis of a cancer; precautions; warnings; indications; clinical or research studies; and/or references. The instructions may be printed directly on the container (when present), or as a label applied to the container, or as a separate sheet, pamphlet, card, or folder supplied in or with the container.

In another embodiment, the disclosure provides an apparatus for determining the expression levels of miR-18b, said apparatus comprising a solid support, wherein a surface of said solid support is linked to an oligonucleotide complementary to miR-18b. In one embodiment, the apparatus is a micro-array. The examples of solid support include, but are not limited to, a glass or nitro-cellulose slide that is used to bind nucleic acids.

The following examples are intended to illustrate but not limit the disclosure. While they are typical of those that might be used, other procedures known to those skilled in the art may alternatively be used.

EXAMPLES

Cell Culture, Plasmids and Transfection

The DO4, WM3211, 1205-Lu, C8161.9, WM278 and Lox melanoma cell lines were obtained and propagated as described in Dar et al., *J Biol Chem* 286:16606-14 (2011). Normal human melanocytes (HEM) were purchased from Lifeline cell technology and grown in LL-0027 media (Lifeline cell technology, Walkersville Md.). Plasmids miR-NASelect™ pEP-miR Null control vector (pEP Null), miR-NASelect™ pEP-hsa-mir-18b expression vector (pEP miR-18b) (Cell Biolabs Inc, San Diego Calif.) were purchased. TaqMan probes for hsa-miR-18b and negative control pre-miR (cont. miR) were purchased from Applied Biosystems (Foster City, Calif.). Sub-confluent cells (60-70% confluent) were treated with 5-AZA-2'-deoxycytidine (5AZA) (Sigma Aldrich, St. Louis Mo.) dissolved in dimethyl-sulfoxide. Cells treated with vehicle served as control. Transient transfections were carried out by Lipofectamine-2000 (Invitrogen Life Technologies, Carlsbad, Calif.) following the manufacturer's protocol.

RNA, DNA and miRNA Extraction from Tissue Samples and Cell Lines.

Samples from melanoma patients (n=92) and benign nevi (n=48) were obtained under a protocol approved by the Institutional Review Board. RNA and miRNA were extracted as previously described in Dar et al., *J Biol Chem* 286:16606-14 (2011).

Quantitative Real Time PCR.

Mature miRNAs and other mRNAs were assayed using the TaqMan MicroRNA Assays and Gene Expression Assays (Applied Biosystems), respectively, as previously described in Dar et al., *J Biol Chem* 286:16606-14 (2011).

Sodium bisulfite modification and sequencing. Methylation status was analyzed within the 2.5 kb region upstream of the miR-18b gene. Bisulfite modification of DNA was performed using the Epi-Tect Bisulfite kit (Qiagen, Valencia Calif.) following the manufacturer's protocol and as previously described in Majid et al., *Carcinogenesis* 30:662-70 (2009). Primers were designed by using the online program Meth Primer (Li et al., *Bioinformatics* 18: 1427-31 (2002)). The methylated and unmethylated specific primers used herein are presented in Table 1:

TABLE 1

| Name | Sequence (SEQ ID NO) |
|---|---|
| MSP-F | GAGGCGTGGGTTTGGCGC (SEQ ID NO: 4) |
| MSP-R | CACCACGCGCTCCAATCCTC (SEQ ID NO: 5) |
| USP-F | TCGTTTTTAATTGGTTTTTATTAGC (SEQ ID NO: 6) |
| USP-R | TCAAAATTTCTTAACAAATATCGTT (SEQ ID NO: 7) |

Cell Viability, Colony Formation and Flow Cytometry.

Cell viability, colony formation and flow cytometry analysis were performed as described previously in Dar et al., *J Biol Chem* 286:16606-14 (2011); and Dar et al., *J Invest Dermatol* 130:2071-9 (2010)).

Western Blot Analysis.

Cell lysates were prepared in PBS containing 1×Halt protease inhibitor cocktail and 1×Halt phosphatase inhibitor cocktail (Pierce, Rockford, Ill.) centrifuged at 3500 r.p.m. for 10 min at 4° C. Proteins (10-15 ug) from each sample were subjected to SDS/polyacrylamide gel electrophoresis (PAGE) and transferred onto a nitrocellulose membrane. Target proteins were detected by using specific antibodies against MDM2, p53, p21, BCL-2 and GAPDH (Santa Cruz Biotechnology, Santa Cruz, Calif.), and PUMA, BCL-XL (Cell Signaling Technology, Danvers, Mass.).

Luciferase Assays.

The 3'-UTR region of MDM2 containing target site sequences complementary to the seed sequence of miR-18b were cloned downstream of the luciferase gene in the pMIR-REPORT luciferase vector (Ambion, Cambridge Mass.), and the resultant vectors were named MDM2-3'UTR. Mutated 3'UTR sequences of MDM2 complementary to miR-18b were cloned in the same vector and the resultant vectors named MDM2-Mut 3'UTR. For reporter assays, cells were transiently transfected with wild-type or mutant reporter plasmid and miR-18b. Firefly luciferase activities were measured by using the Dual Luciferase Assay (Promega, Madison, Wis.) 48 hr after transfection and the results were normalized with *Renilla luciferase*. Each reporter plasmid was transfected at least three times (on different days) and each sample was assayed in triplicate.

Invasion and Migration Assay.

For 1205-Lu cells boyden chamber inserts were coated with 15 μl matrigel at 6 mg/ml protein. For migration assay boyden chamber inserts were not coated and cells were directly added to them.

Stable Cell Generation and In Vivo Study.

1205-Lu cells were transfected with pEP Null or pEP miR-18b vectors (Cellbiolabs, San Diego Calif.) and selected with puromycin (1 μg/mL). For in-vivo studies as described previously in Dar et al., *J Invest Dermatol* 130: 2071-9 (2010), $1 \times 10^6$ cells were injected into nude mice subcutaneously and tumor growth was followed for 24 days. All animal care was in accordance with the institutional guidelines.

Immunofluorescence Assay.

1205-Lu cells were plated in 8-well plate chamber. Immunofluorescence assay was performed as previously described in Dar et al., *Oncogene* 28: 866-75 (2009). N-cadherin, vimentin, slug and E-cadherin antibodies (Cell signaling) were used in the assay.

Chromatin Immunoprecipitation Analysis.

Chromatin immunoprecipitation analysis was performed using the EZ-ChIP kit (Upstate Biotechnology, Charlottesville, Va.) according to the manufacturer's directions and as described in Majid et al., *Carcinogenesis* 30: 662-70 (2009). Antibodies used in the immunoprecipitations were purchased from Upstate Biotechnology and Ambion (Austin, Tex.) and were specific for acetyl histone H3 (06-599), acetyl histone H4 (06-866), dimethyl-histone H3 lysine 4 (07-030), trimethyl-histone H3 lysine 4(07-473), dimethyl-histone H3 lysine 9 (07-441) and trimethyl-histone H3 lysine 9 (ab8898). The immunoprecipitated DNA was eluted in a total volume of 50 μl and 2 μl were used for PCR. The sequence of primers used for PCR is presented in Table 2:

TABLE 2

| Orientation | Sequence from 5' to 3' (SEQ ID NO) |
|---|---|
| Forward | GCTTGAATGGAGAACTCCG (SEQ ID NO: 8) |
| Reverse | CTTACCTAATGCTCCCGTTGA (SEQ ID NO: 9) |

Statistical Analysis.

All quantified data represents an average of at least triplicate samples or as indicated. Error bars represent standard error of the mean. Statistical significance was determined by the Student's t-test and two-tailed p values <0.05 were considered significant. Kaplan-Meier analysis (log-rank test) was performed by using Prism 5 software (Graphpad Software Inc., CA).

miR-18b Expression in Melanocytes and Melanoma Cells.

The expression pattern of miRNAs in melanoma was determined by performing a miRNA microarray on a small number of nevi (n=5) and melanoma tumor samples (n=10) using the Agilent platform. miR-18b was found to be significantly downregulated in melanoma samples as compared to nevi. To validate the microarray results, miRNA-quantitative RT-PCR (miR qRT-PCR) analysis was performed on an independent cohort of nevus and melanoma tissues. miR qRT-PCR of nevus (n=48) and melanoma (n=92) samples indicated that miR-18b expression is significantly downregulated in melanomas when compared to nevi (see FIG. 1A).

Figure 1B:
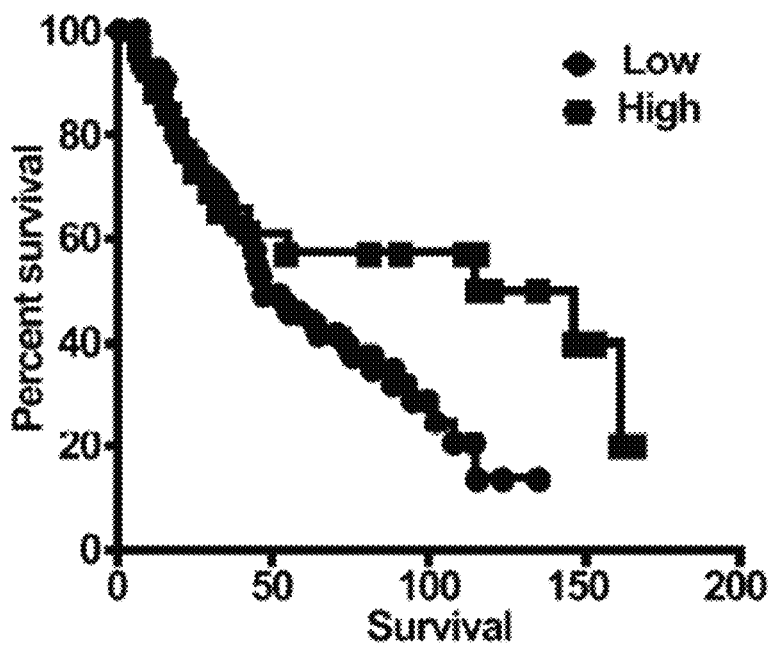
Figure 1C:
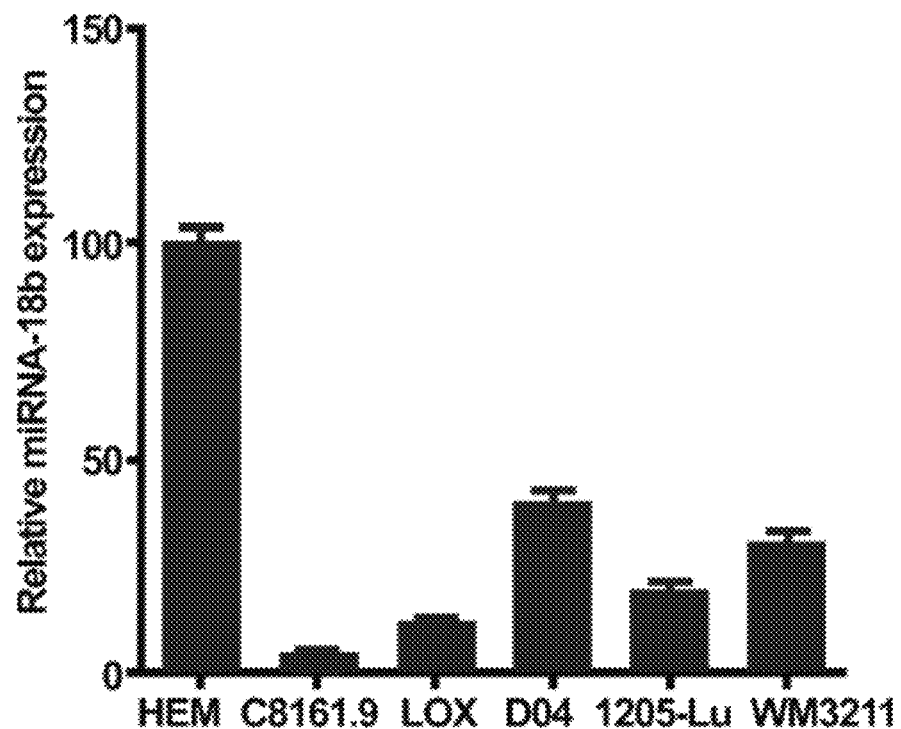

By performing Kaplan-Meier analysis, low levels of miR-18b in primary cutaneous melanoma specimens were found to be associated with a significantly reduced overall survival rate (see FIG. 1B, p<0.04). The expression levels of miR-18b in a panel of human melanoma cell lines and normal melanocytes were then determined. The results indicate that there was a significant downregulation in expression of miR-18b in melanoma cells as compared to normal melanocytes (see FIG. 1C). Accordingly, the data suggest that miR-18b is downregulated in specimens and cell lines containing melanoma cells, and that by measuring miR-18b expression levels from a subject would enable a medical practitioner to evaluate the progression or stage of the melanoma in the subject.

miR-18b is Silenced in Melanoma Through CpG Hypermethylation.

Figure 2A:
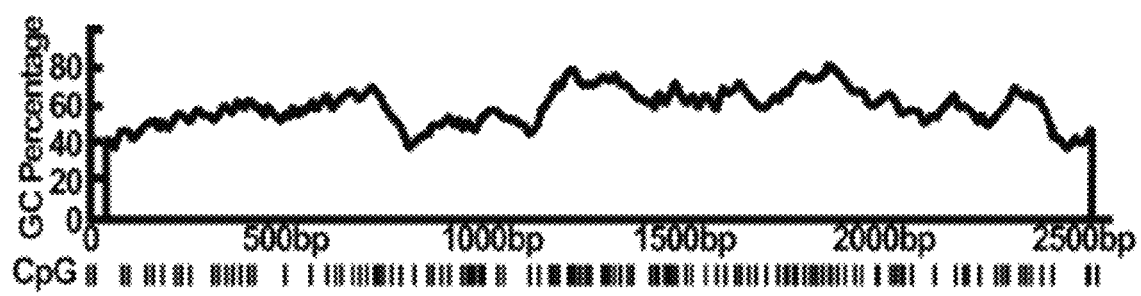
FIG. 2A-D shows miR-18b expression is suppressed by hypermethylation. (A) Schematic representation of the upstream region (2500 bp) of miR-18b analyzed for methylation, with CpG sites represented by vertical lines. (B) miR-18b expression, as determined by qRT-PCR, was upregulated in five melanoma cell lines (C8161.9, LOX, 1205-Lu, DO4 and WM278) following 5AZA treatment. (C) miR-18b promoter methylation status in melanoma cell lines and thirty tumor samples; M, amplified product with primers recognizing methylated sequence; U, amplified product with primers recognizing unmethylated sequence. (D) Chromatin immunoprecipitation assay performed on cells after miR-18b overexpression. miR-18b overexpression resulted in the enrichment of active chromatin modifications (acetyl Histone H3, H4 and methyl-2H3K4) and the reduction of repressive modifications (2H3K9 and 3H3K9).
Figure 2B:
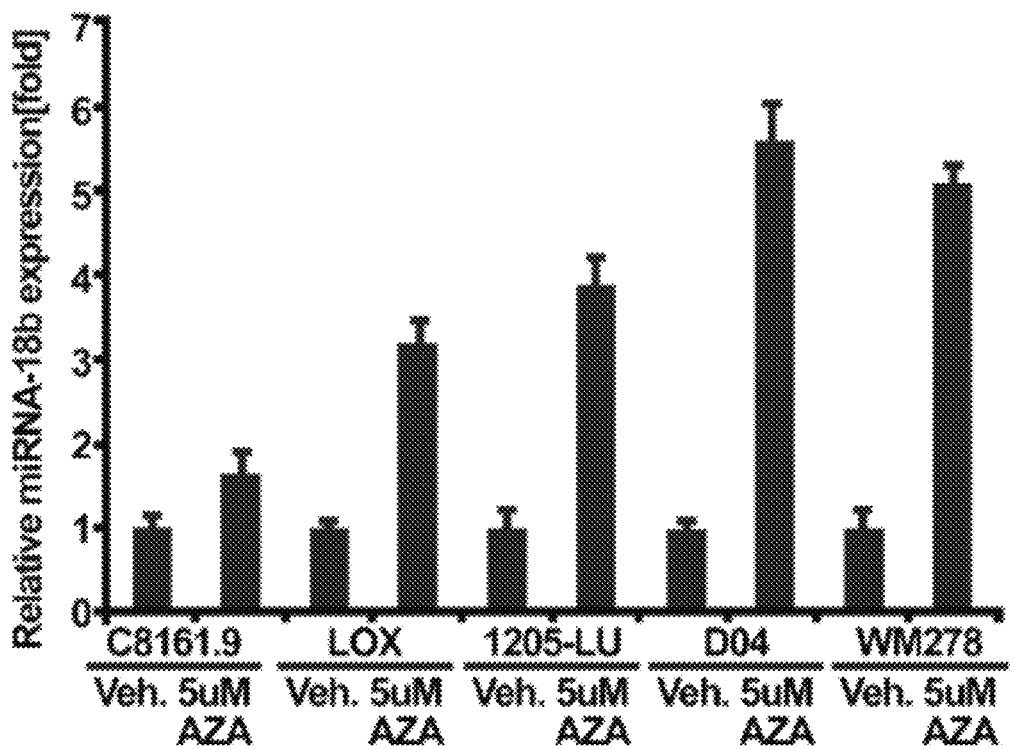
Figure 2C:
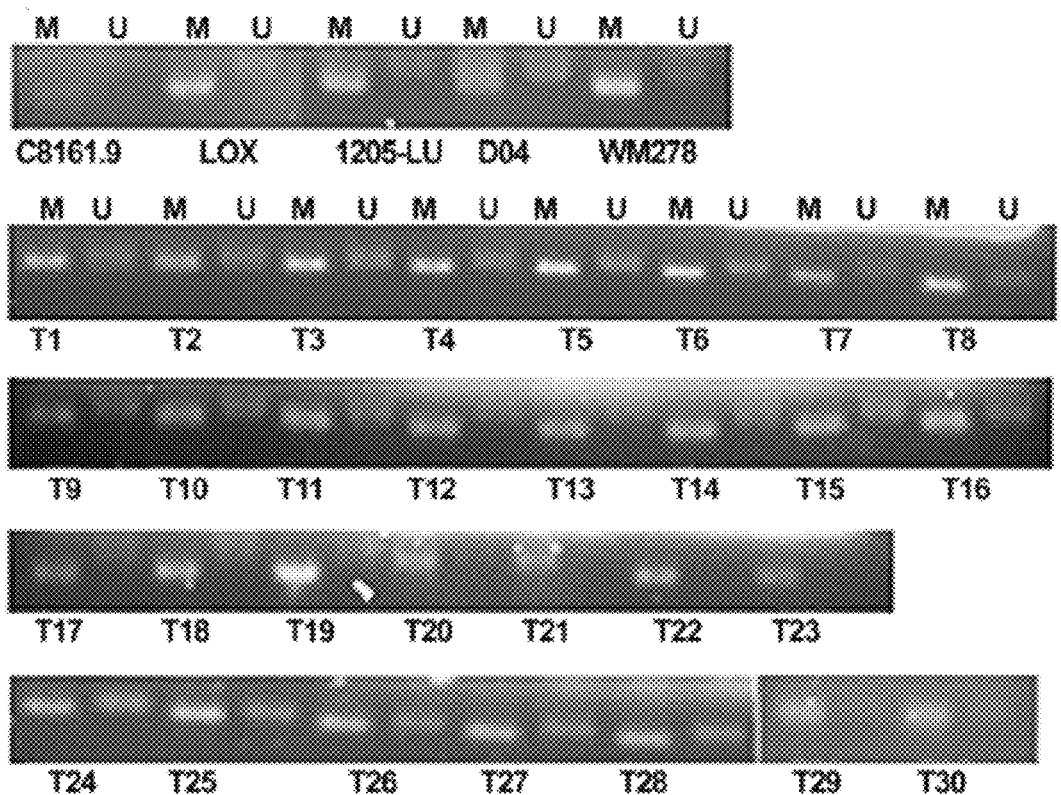
Figure 2D:
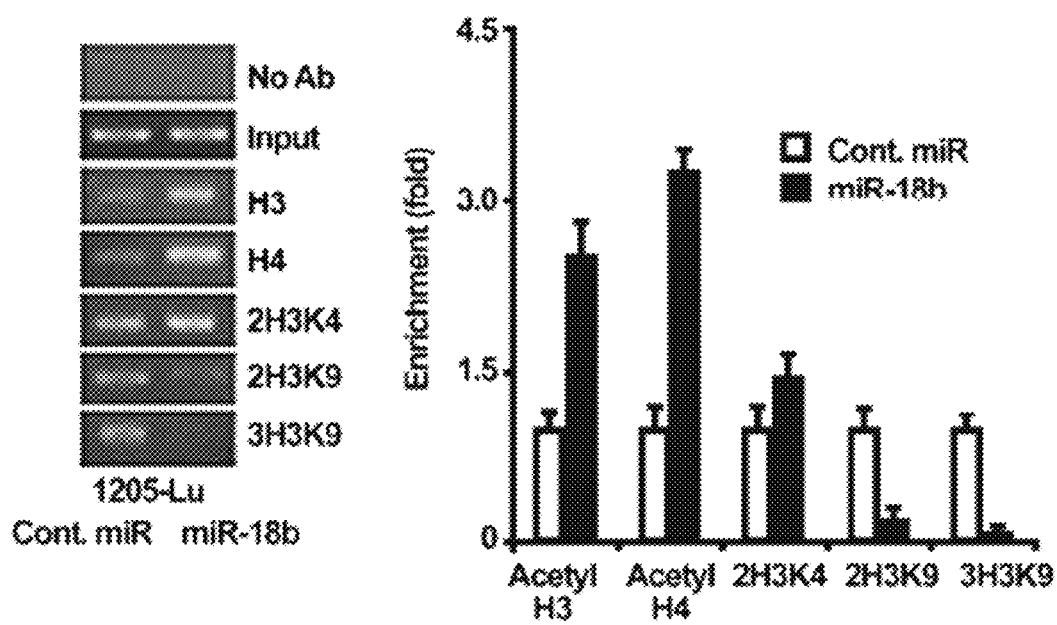

To understand the mechanism underlying the suppression of miR-18b expression in melanoma, methylation analyses of the 2.5 kb sequence upstream of miR-18b were performed. By employing the methprimer software, a number of CpG rich regions were observed (see FIG. 2A). Furthermore, treatment of five melanoma cells lines with the demethylating agent 5-Aza-deoxycitidine (5AZA, 5 μM) resulted in significant upregulation of miR-18b expression, suggesting a possible role for methylation in its suppression (FIG. 2B). To investigate the methylation status of melanoma cell lines and tumor samples, primers were designed targeting methylated and unmethylated miR-18b. As shown in FIG. 2C, a distinct methylated band was observed in five melanoma cell lines and thirty tumor samples. By contrast, the unmethylated band in melanoma cell lines and tumor samples was either absent or weak. To determine whether there were covalent chromatin modifications following miR-18b overexpression, chromatin immunoprecipitation analysis was performed. miR-18b overexpression resulted in enrichment of acetylated histones H3, H4 and H3 di-methylated lysine 4 (see FIG. 2C-D), indicative of gene activation. Conversely, suppression of repressive chromatin modifications (2H3K9 and 3H3K9) following miR-18b overexpression was observed (see FIG. 2C-D). These findings demonstrate that miR-18b is silenced by hypermethylation in melanoma cell lines and tumor samples, and that its overexpression is associated with enrichment of active histone modifications. Accordingly, the data suggest that by preventing, inhibiting or reversing the hypermethylation of miR-18b in melanoma cells could provide a therapeutic beneficial effect in subjects with melanoma.

MDM2 as a Target of miR-18b.

Figure 3A:
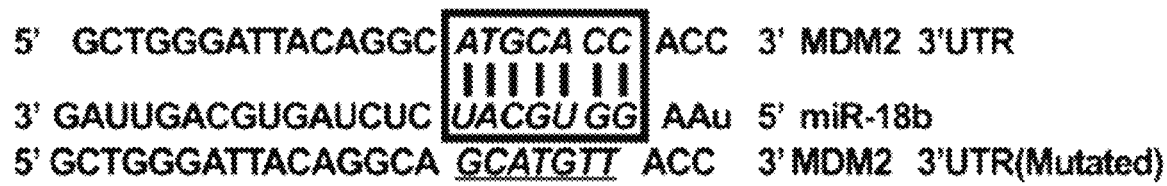
FIG. 3A-F shows MDM2 as a direct target of miR-18b, and inverse correlation of miR-18b and MDM2 in melanoma cells. (A) The miR-18b seed sequence (SEQ ID NO:1) is complementary to the 3'UTR of MDM2 (SEQ ID NOs:10 and 11). (B) MDM2 expression at the mRNA and protein levels in different human melanoma cell lines and normal melanocytes. (C) and (D) Duplicate luciferase assays, showing decrease in reporter activity after co-transfection of MDM2-3'UTR with miR-18b in 1205-Lu cells and LOX cells respectively. The mutant 3UTR had no effect on reporter activity. (E) Relative miR-18b expression level in 1205-Lu cells after transfection with miR-18b as determined by miR qRT-PCR. (F) Western blot analysis showing suppression in MDM2 and upregulation in p53, p21 and PUMA at protein levels. Wherein, * is p<0.05.
Figure 3B:
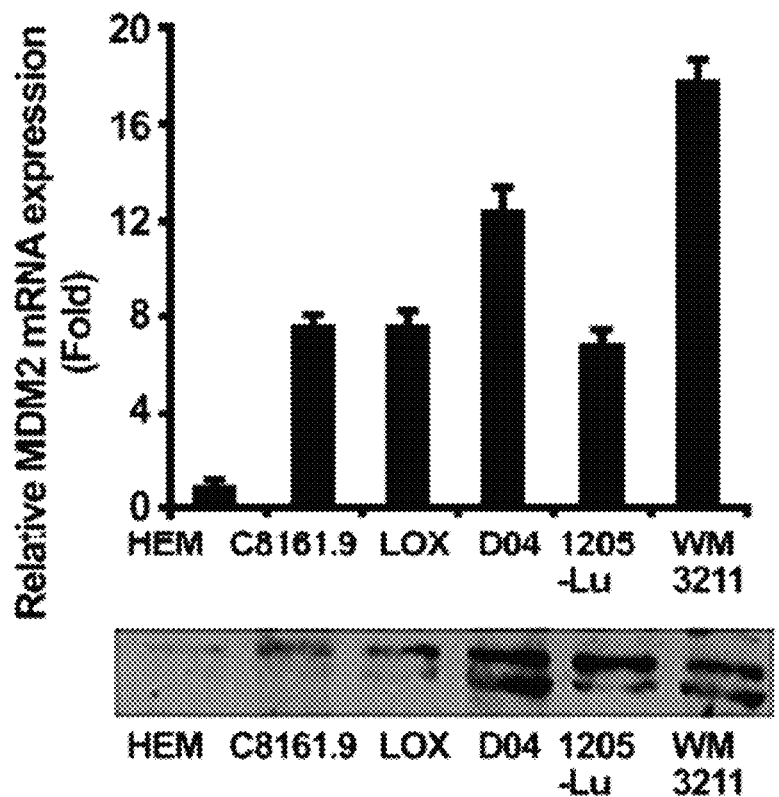

To identify potential effectors of miR-18b, we used various algorithms that predict mRNA targets, and identified MDM2 as a putative target, as the seed sequence of miR-18b was complementary to the 3'UTR of MDM2 (See FIG. 3A). To investigate the correlation between expression of miR-18b and that of MDM2, MDM2 expression at the mRNA and protein levels in the same panel of cell lines was determined. MDM2 expression levels were higher in melanoma cells when compared to the normal melanocyte line (see FIG. 3B), although the absolute level of expression varied among different melanoma cell lines. These data demonstrate an inverse correlation between the expression of miR-18b and that of MDM2, suggesting MDM2 as a target of miR-18b.

Figure 3C:
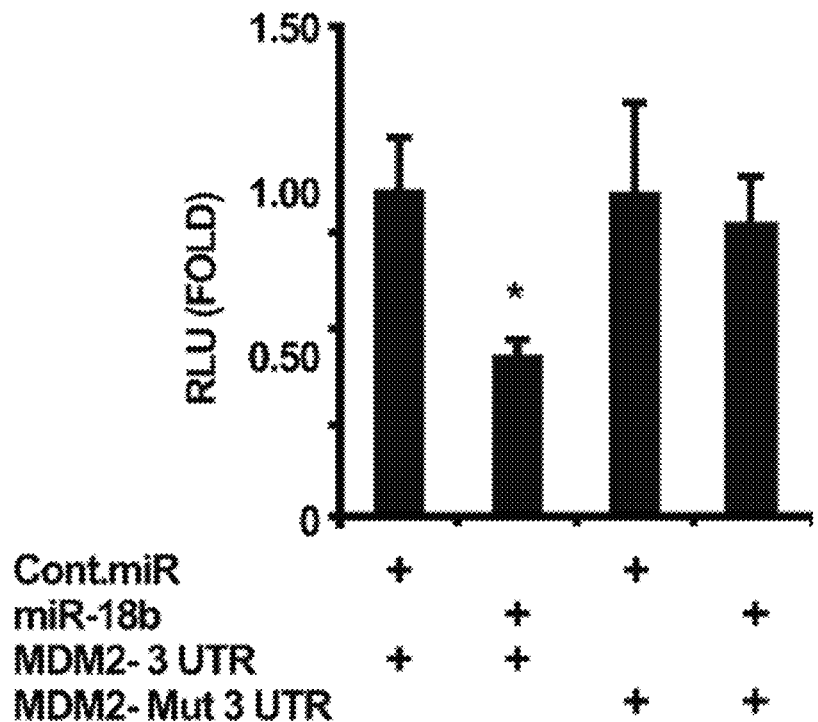
Figure 3D:
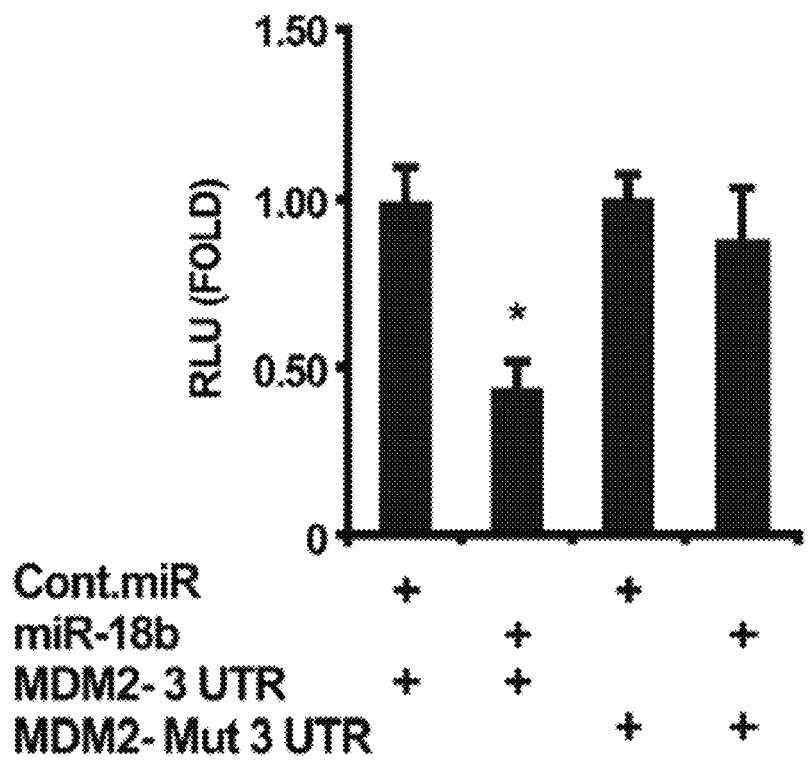
Figure 3E:
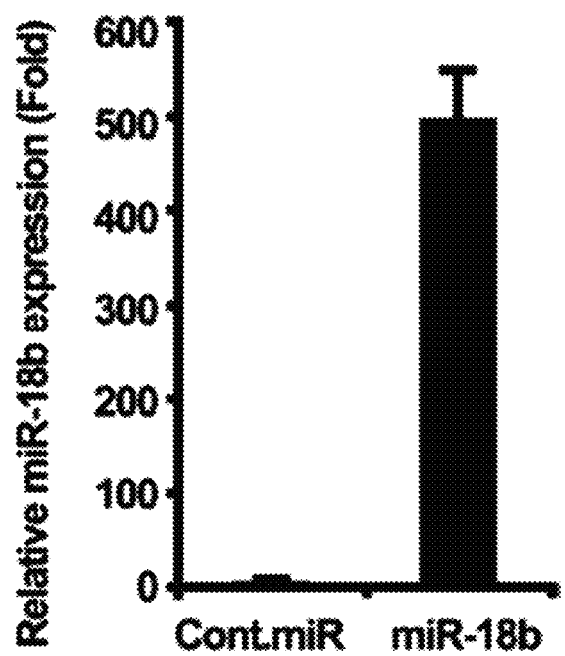
Figure 3F:
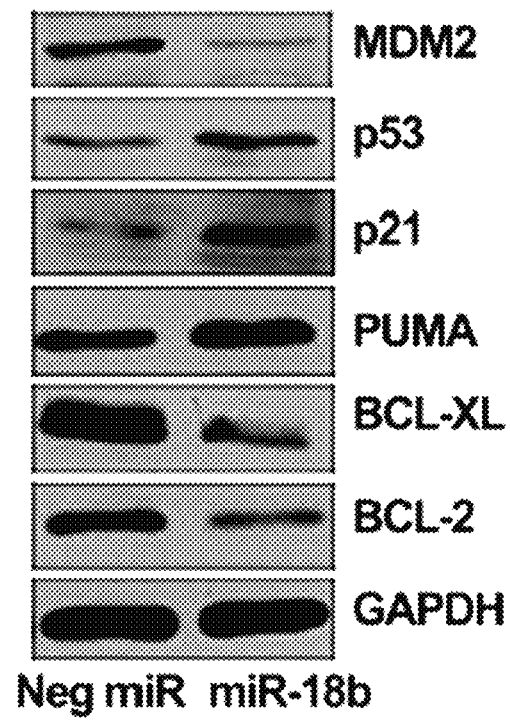

Next, the 3'UTR of MDM2 harboring the complementary sequence to the miR-18b seed sequence was cloned in a reporter plasmid vector. In parallel, a mutated 3'UTR sequence was cloned in the same reporter plasmid. Transient co-transfection of the MDM2-3'UTR construct along with miR-18b into human 1205-Lu and LOX melanoma cells led to a significant decrease in reporter expression when compared with the control vector (See FIG. 3C-D). These results indicate that the conserved nucleotides in the 3'UTR of MDM2 were responsible for miR-18b targeting in vitro. Transient miR-18b overexpression (see FIG. 3E) significantly suppressed MDM2 at the protein level, with a concomitant upregulation of the pro-apoptotic genes p53 and PUMA, and downregulation of the anti-apoptotic genes BCL2 and BCL-XL) (see FIG. 3F). Intriguingly, miR-18b overexpression had no effect on cell survival, MDM2 and p53 expression levels in C8161.9 melanoma cell lines that harbor mutant p53 in contrast to 1205-Lu and LOX, which have wild type p53. Cisplatin induced expression of miR-18b, and melanoma cells treated with miR-18b showed enhanced sensitivity to cisplatin cytotoxicity. Taken together, these results demonstrate MDM2 (and the p53 pathway) as a target of miR-18b action in melanoma.

miR-18b Regulates Melanoma Cell Proliferation, Colony Formation and Apoptosis.

Figure 4A:
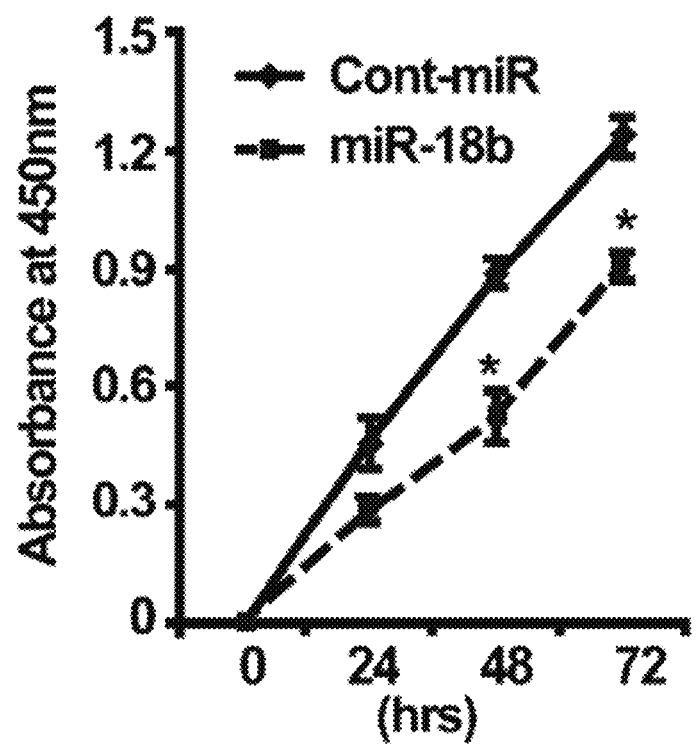
FIG. 4A-F miR-18b inhibits 1205-Lu melanoma cell proliferation, colony formation, and induces apoptosis. (A) The proliferative ability of 1205-Lu cells after miR-18b transfection is significantly reduced when compared to cont. miR. (B) miR-18b overexpression significantly inhibits the colony formation ability of 1205-Lu melanoma cells. (C) Cell cycle analysis showing significant decrease in the S-phase of 1205-Lu cells overexpressing miR-18b. (D) miR-18b overexpression significantly induced apoptotic in 1205-Lu cells as compared to cont. miR expressing cells. (E-F) MDM2 co-transfection along with miR-18b reversed suppression in cell proliferation, expression level of p53, p21 and PUMA. *p<0.05.
Figure 4B:
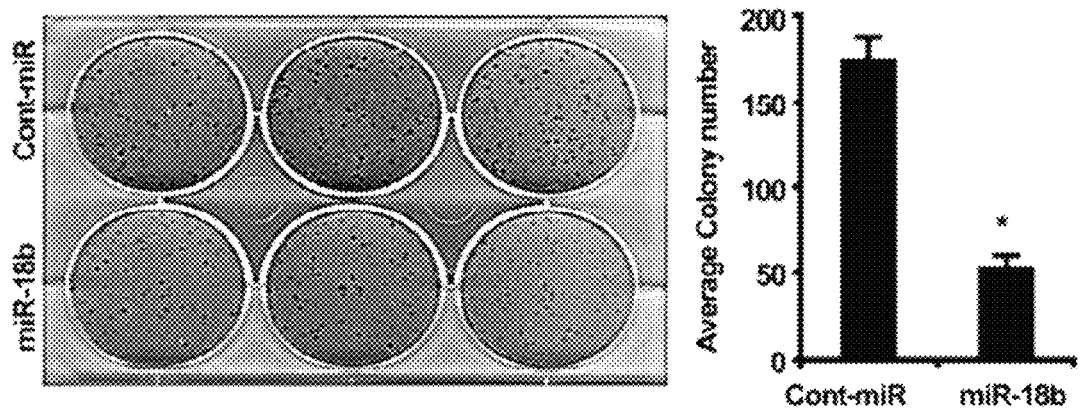
Figure 4C:
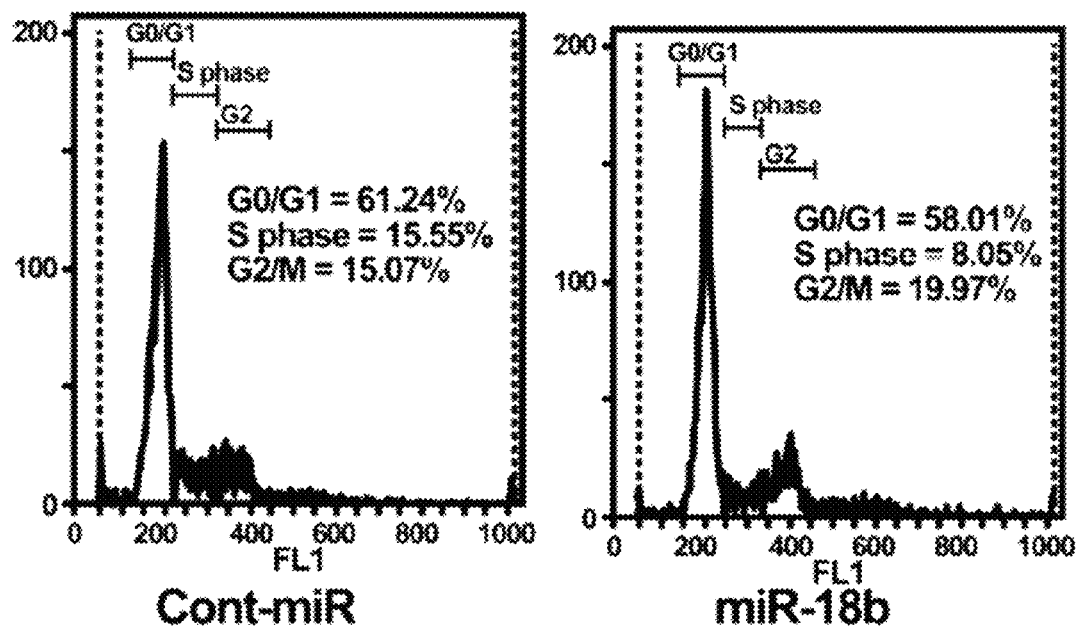
Figure 4D:
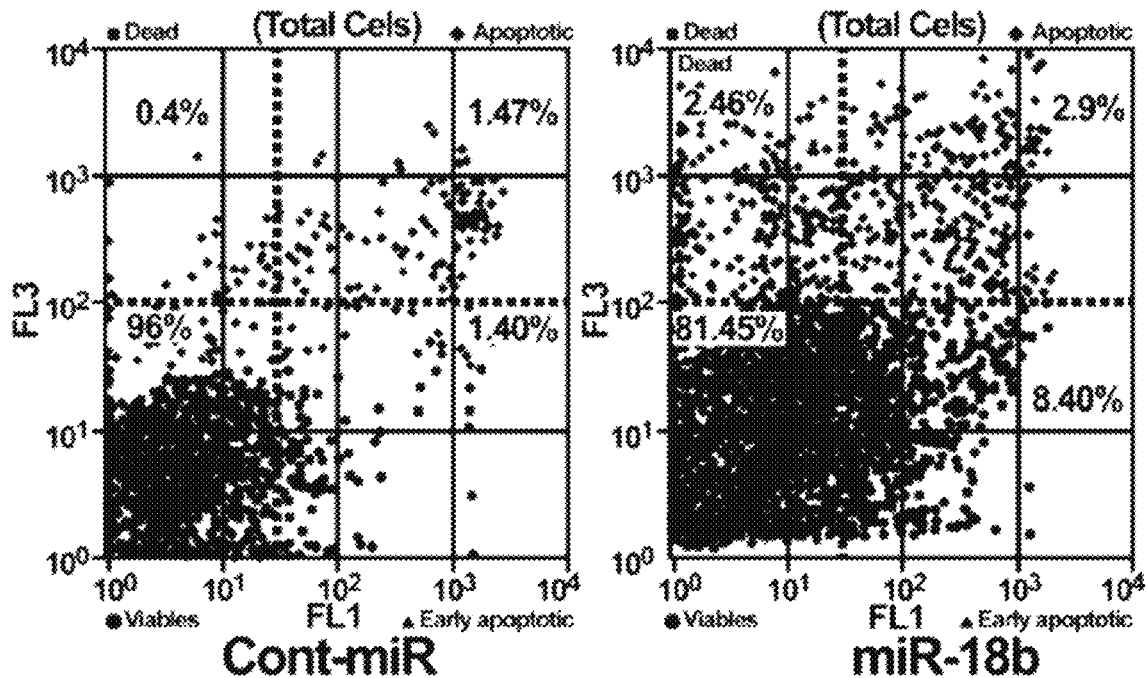
Figure 4E:
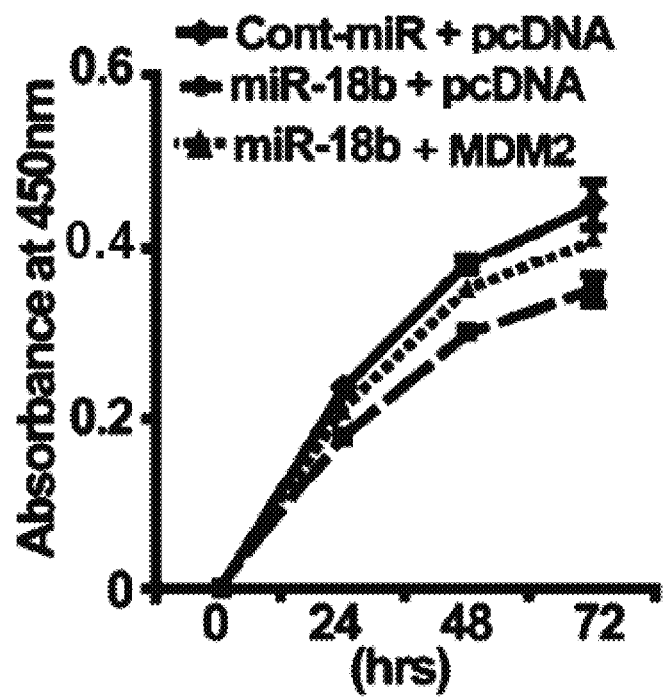
Figure 4F:
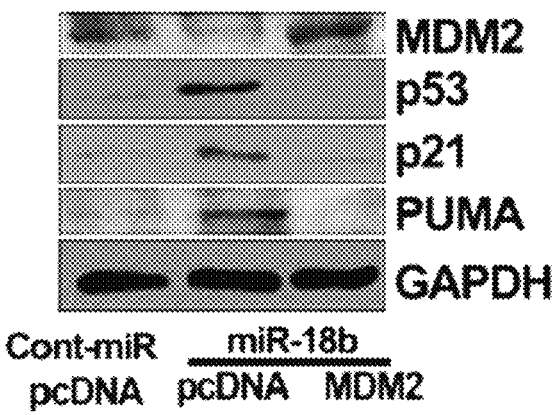
Figure 5A:
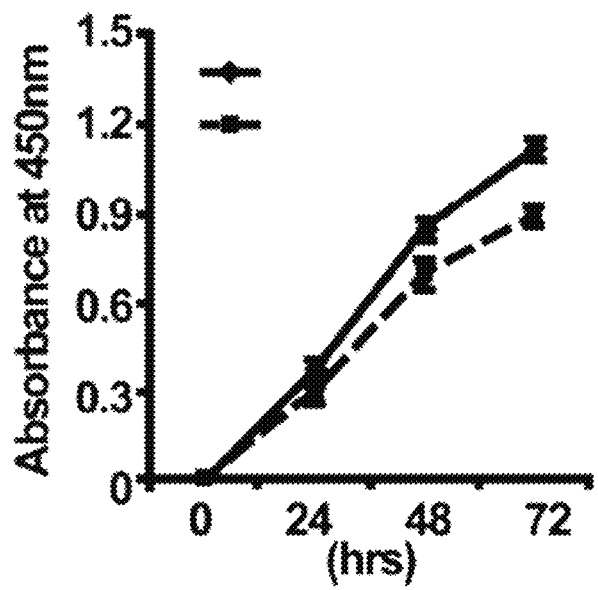
FIG. 5A-E shows In transfected LOX cells, miR-18b suppresses melanoma cell proliferation and induces apoptosis in melanoma cells. (A) The proliferative ability of LOX cells after miR-18b transfection is significantly reduced as compared to cont.miR. (B) miR-18b overexpression significantly inhibits the colony formation ability of melanoma cells. (C) Western blot showing that MDM2, BCL2, and BCL-XL expression is downregulated in LOX cells transfected with miR-18b versus Cont.miR, while p53, p21, and PUMA expression is upregulated in LOX cells transfected with miR-18b versus cont.miR. GAPDH is provided as a control. (D) Cell cycle analysis showing significant decrease in the S-phase of LoX cells overexpressing miR-18b. (E) Apoptosis assays showing an increased number of apoptotic cells in the LOX cells transfected with miR-18b versus LOX cells transfected with cont.miR.
Figure 5B:
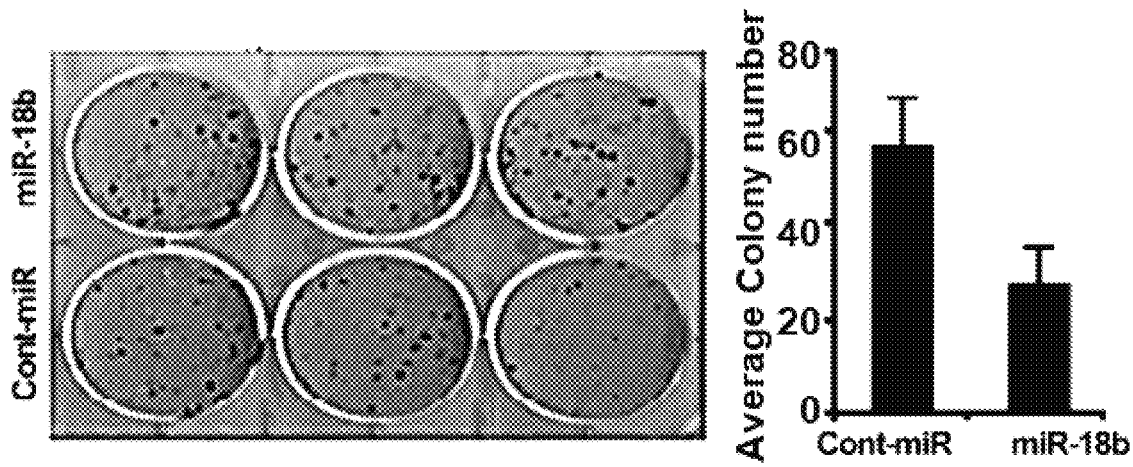
Figure 5C:
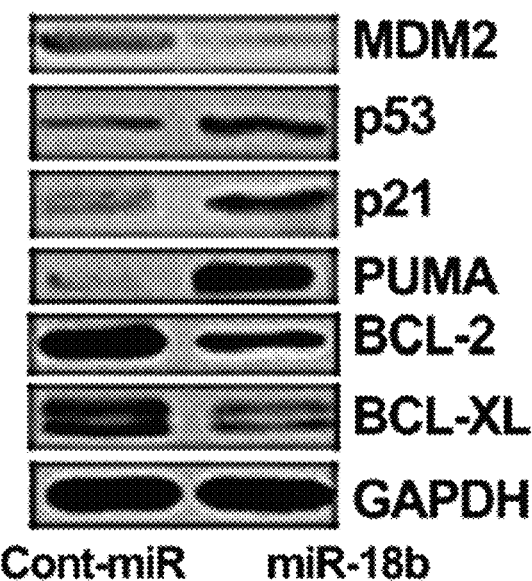
Figure 5D:
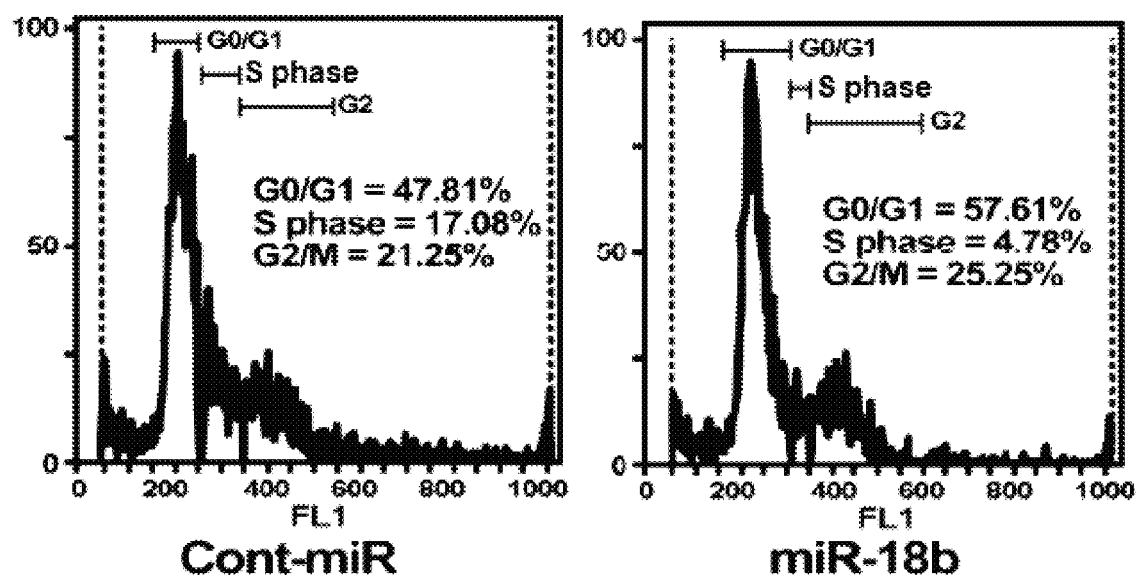
Figure 5E:
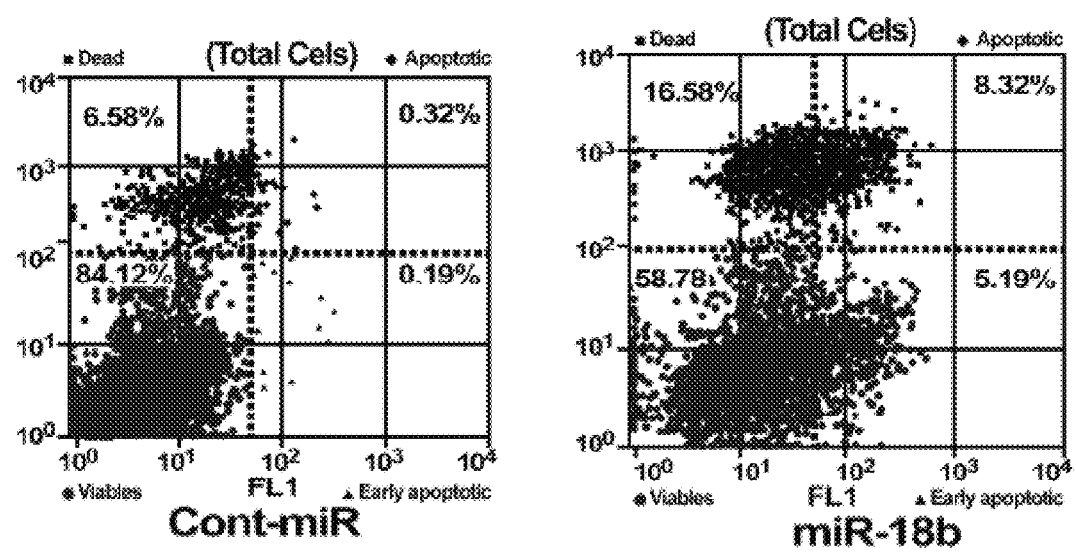

The functional effects of miR-18b-driven downregulation of MDM2 and the subsequent induction of pro-apoptotic genes were then assayed. Transient transfection of 1205-Lu cells with miR-18b resulted in significantly decreased cell proliferation over time (see FIG. 4A) as compared to cells expressing a control miR sequence (cont.miR). The effects of miR-18b on melanoma cell viability were then examined by using a colony formation assay. The miR-18b-transfected 1205-Lu cells showed low colony formation ability, as both the size and number of foci in miR-18b expressing cells were suppressed when compared to cont.miR-expressing cells (see FIG. 4B). Cell cycle analysis revealed a significant decrease in the S-phase (15.5% to 8.05%, p<0.02) of 1205-Lu cells overexpressing miR-18b as compared to cont. miR-expressing cells (see FIG. 4C). miR-18b overexpression induced apoptosis in 1205-Lu cells as compared to cont.miR (2.87% to 11.30%, p<0.01) (see FIG. 4D). To confirm the effect of miR-18b on melanoma cell proliferation and apoptosis, miR-18b was transfected into LOX human melanoma cells. As shown in FIG. 5 A-D, there was a significant decrease in cell proliferation, colony formation and S-phase, along with an increase in apoptosis, in LOX cells transfected with miR-18b. These results confirm the phenotypic effects of miR-18b overexpression in human melanoma cells.

The Effects of miR-18b Overexpression on Melanoma Cells is Mediated by Regulation of MDM2 Expression.

To further explore the role of MDM2 as a target of miR-18b, 1205-Lu cells were co-transfected with miR-18b as well as MDM2, and its effects on gene expression and melanoma cell survival were examined. Co-transfection of miR-18b and an empty vector control resulted in suppression of MDM2, activation of the p53 pathway, and suppressed melanoma cell survival, when compared with co-transfection of the cont. miR and empty vectors. These effects were largely reversed following co-transfection of the miR-18b and MDM2-expressing vectors. These results indicate that the effects of miR-18b on downstream gene expression and melanoma cell proliferation are mediated largely by its inhibition of MDM2 expression.

Stable Overexpression of miR-18b Inhibits Cell Survival, Colony Formation, and In Vivo Tumor Cell Growth.

Figure 6A:
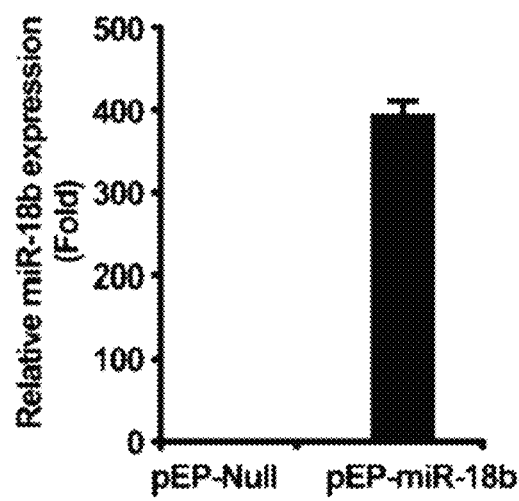
FIG. 6A-H shows stable overexpression of miR-18b inhibits cell proliferation in vitro and in vivo. (A) Relative miR-18b expression levels in 1205-Lu cells stably expressing miR-18b as determined by miR qRT-PCR. (B) Stable overexpression of miR-18b in melanoma cell lines significantly suppressed cell proliferation. (C) Colony formation ability is significantly reduced by miR-18b. (D) Stable expression of miR-18b suppresses the S-phase of the cell cycle. (E) Stable miR-18b overexpression induces apoptosis in 1205-Lu cells. (F) Western blot analysis showing suppression of MDM2 and upregulation of p53, p21 and PUMA. (G) Tumor volume following subcutaneous injection of 1205-Lu cells expressing miR-18b was significantly reduced when compared with cont.miR-expressing cells (N=10 mice per group). (H) Western blot showing expression of MDM2 from subcutaneous tumors expressing cont.miR and miR-18b. Wherein, * is p<0.05.
Figure 6B:
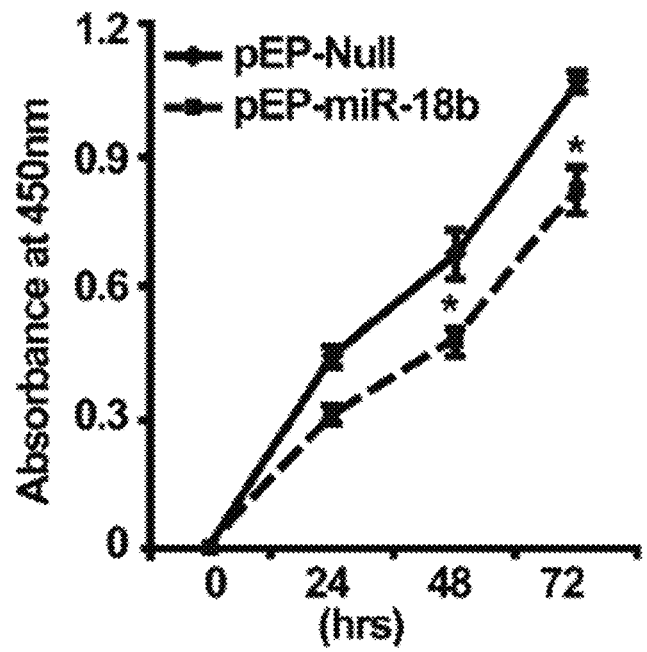
Figure 6C:
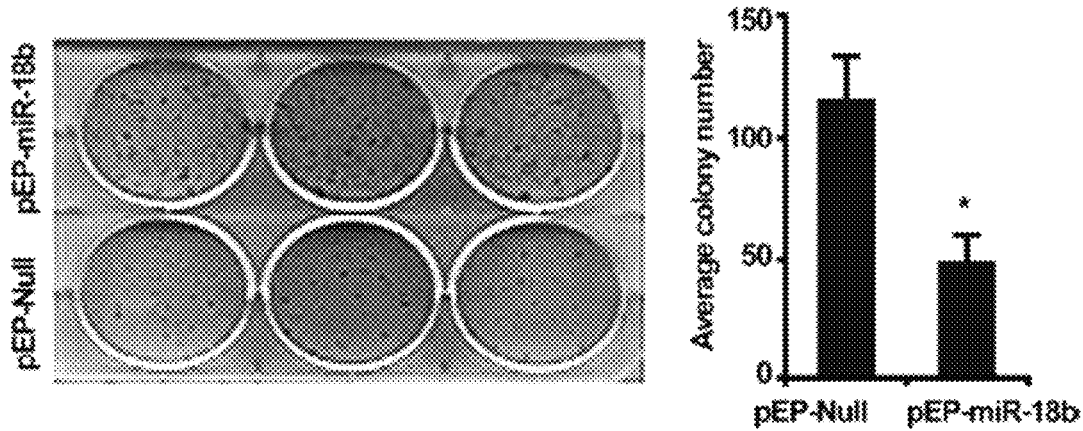
Figure 6D:
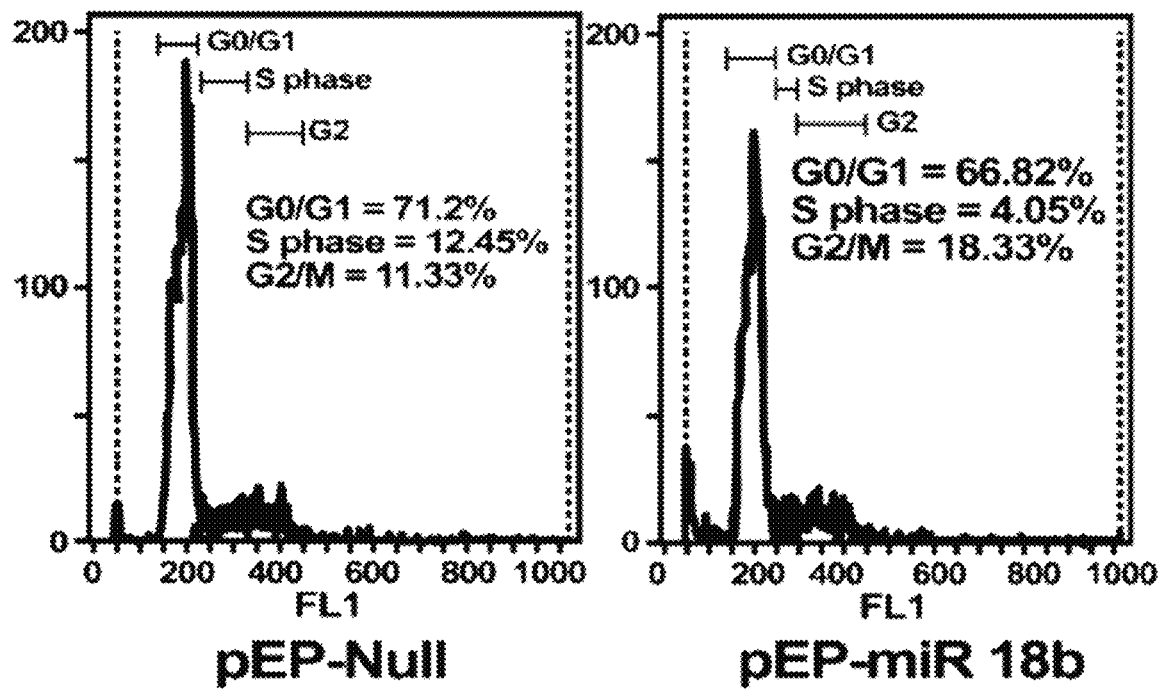
Figure 6E:
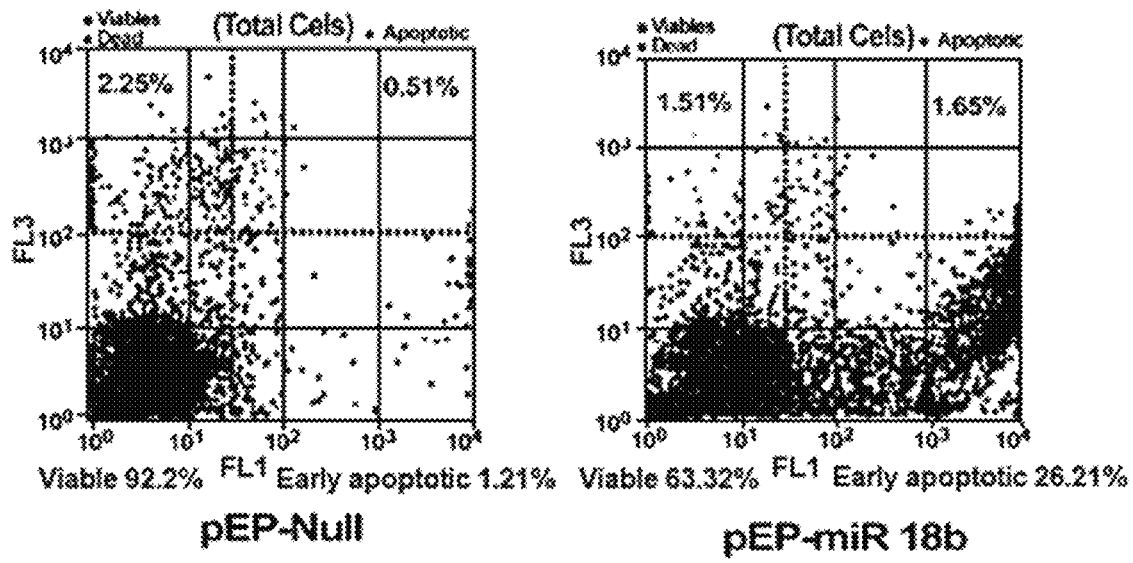
Figure 6F:
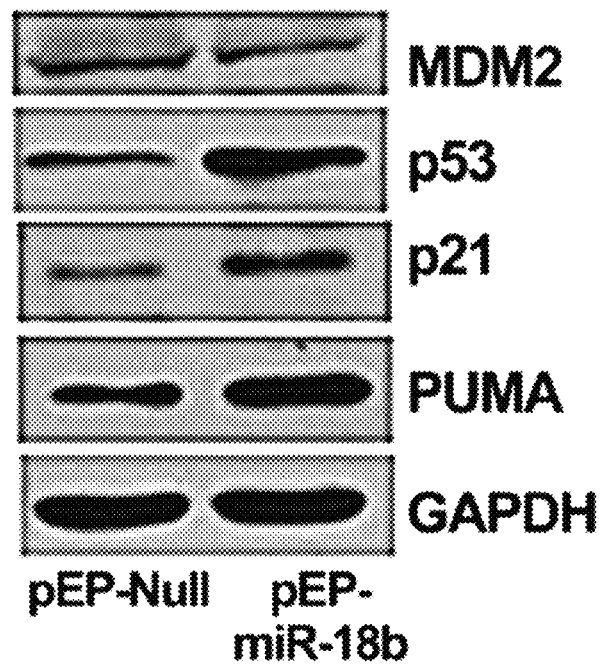
Figure 6G:
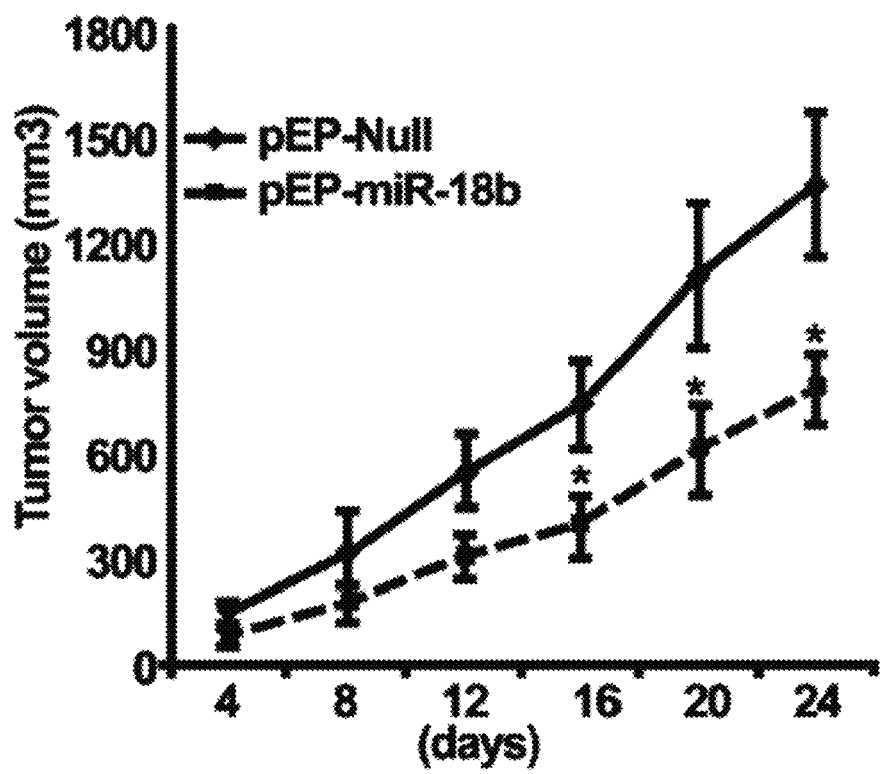
Figure 6H:
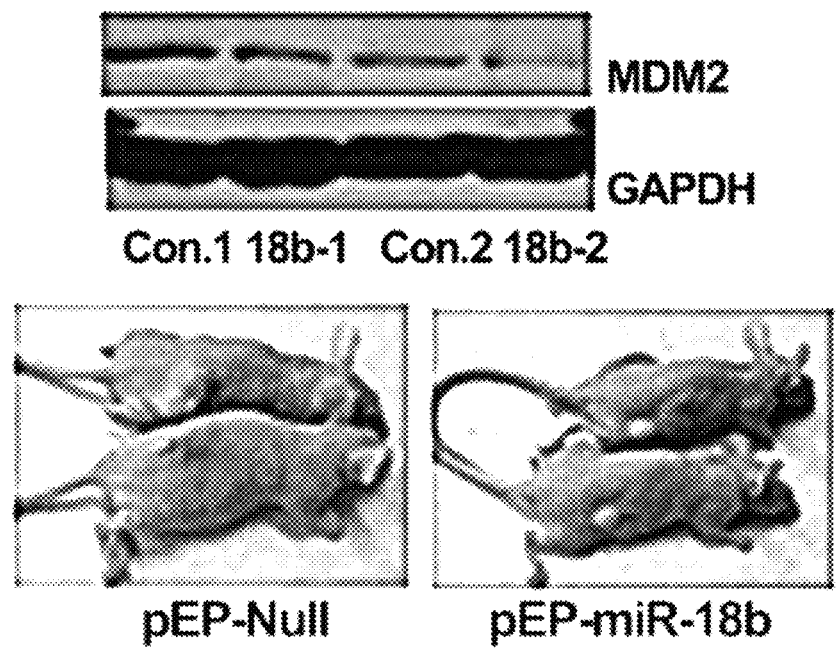

The effects of stable expression of miR-18b in melanoma were then studied. 1205-Lu cells stably expressing miR-18b were generated, and overexpression of miR-18b was confirmed by miR qRT-PCR analysis (see FIG. 6A). The cell proliferation of 1205-Lu cells expressing miR-18b was significantly suppressed in comparison to control vector-expressing cells (see FIG. 6B). miR-18b overexpressing cells had significant decreases in colony formation (see FIG. 6C) and cells in S-phase (see FIG. 6D) as compared to control vector-expressing cells. miR-18b overexpression resulted in a significant increase in the apoptotic index of 1205-Lu cells (see FIG. 6E). In addition, MDM2 was significantly downregulated in miR-18b overexpressing cells, with a concomitant increase in expression of p53 and PUMA (see FIG. 6F). Stable overexpression of miR-18b significantly suppressed tumor growth in vivo upon subcutaneous inoculation into nude mice in comparison to cells expressing control vector (see FIG. 6G). MDM2 was suppressed at the protein level in miR-18b-overexpressing tumors in comparison with control tumors (see FIG. 6H). These results confirm that miR-18b is a tumor suppressor and has beneficial effects on the MDM2-p53 axis. Moreover, the results demonstrate that therapies comprising polynucleotides comprising miR-18b and/or agents which enhance miR-18b expression can be effective in treating cancer.

Cisplatin Induces miR-18b Expression.

Figure 7A:
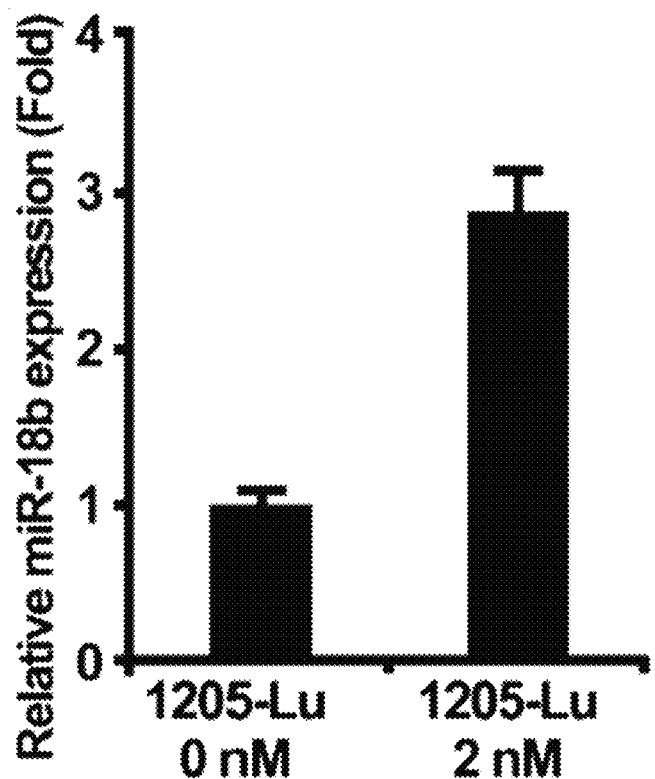
FIG. 7A-B shows cisplatin induces miR-18b. (A) Cisplatin induces expression of miR-18b as determined by qRT-PCR after 48 hrs of treatment. (B) Overexpression of miR-18b and cisplatin treatment resulted in greater suppression of the proliferative ability of melanoma cells than treatment with cisplatin alone.
Figure 7B:
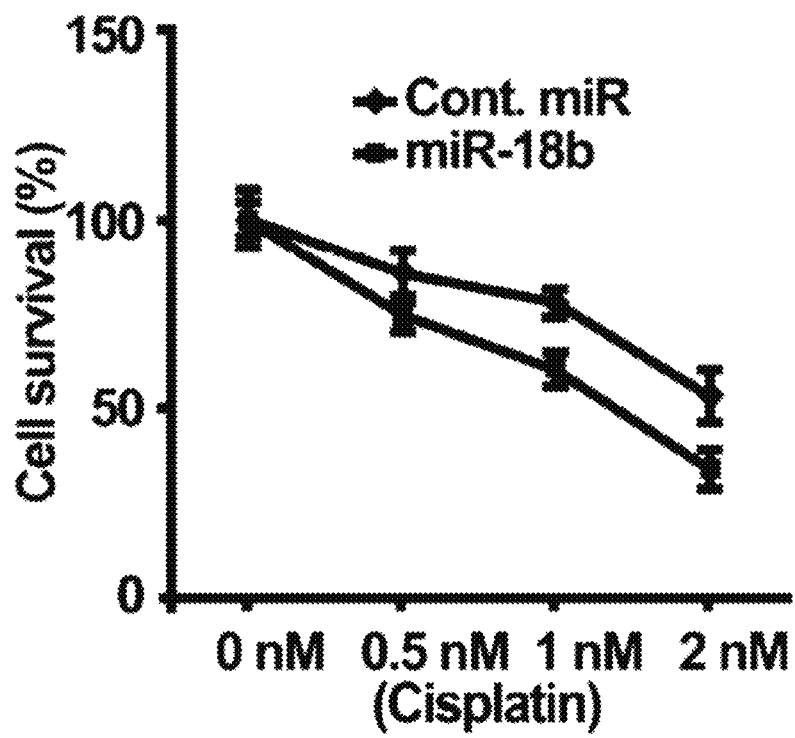

Melanoma cells are highly resistant to conventional chemotherapeutic agents. Given that miR-18b upregulated expression of p53 via MDM2, and given the known effects of p53 in mediating chemotherapy-induced apoptosis (Li et al., *Melanoma Res* 8:17-23 (1998)), the potential interaction between chemotherapeutic agents and miR-18b expression was investigated. Treatment of 1205-Lu cells with 2 nM cisplatin for 48 hr resulted in significantly upregulated miR-18b expression as compared to vehicle-treated cells (see FIG. 7A). In addition, overexpression of miR-18b and cisplatin treatment resulted in suppressing the proliferation of melanoma cells to a significant extent (see FIG. 7B). Moreover, the results demonstrate that a synergist effect in treating cancer can be reached by combining therapies based on elevating miR-18b levels in a subject with other known anti-cancer agents.

miR-18b Suppresses Melanoma Cell Migration and Invasiveness, and Reverses Epithelial-to-Mesenchymal-Transition (EMT).

Figure 8A:
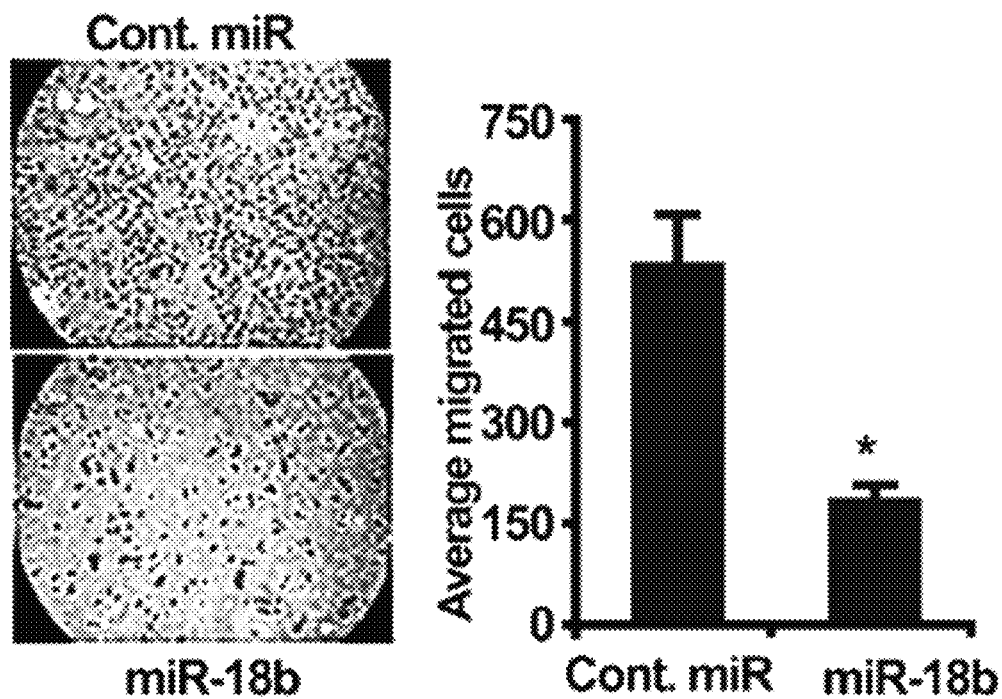
FIG. 8A-E shows miR-18b suppresses melanoma cell migration and invasiveness, and reverses epithelial-to-mesenchymal-transition (EMT). (A) and (B) Duplicate experiments, showing miR-18b overexpression significantly suppresses migratory ability and invasiveness of 1205-Lu melanoma cell lines as compared to cont.mir expressing cells. (C) and (D) Immunofluorescence assays demonstrating that miR-18b overexpression in 1205-Lu melanoma cells downregulates the expression of vimentin, and N-cadherin. DAPI (4',6-Diamidino-2-phenylindole) indicates the location of DNA in the cell. (E) Western blot showing that N-Cadherein, Vimentin and Slug expression is downregulated in 1205-Lu melanoma cells transfected with miR-18b versus cont.miR, while E-Cadherein expression is upregulated in 1205-Lu melanoma cells transfected with miR-18b versus cont.miR. GAPDH is provided as a control for transfection.
Figure 8B:
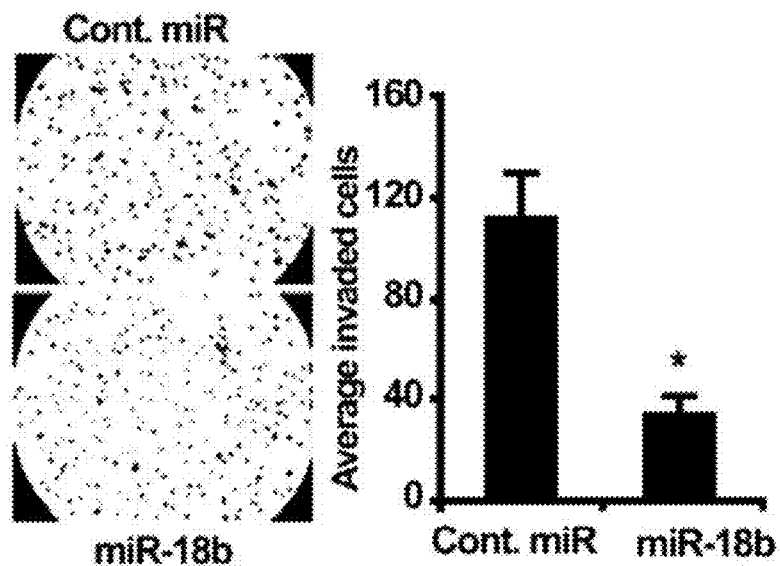
Figure 8C:
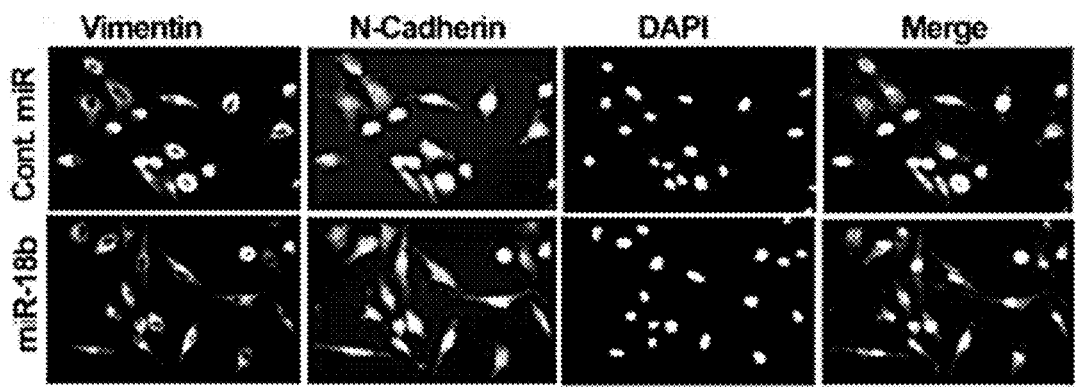
Figure 8D:
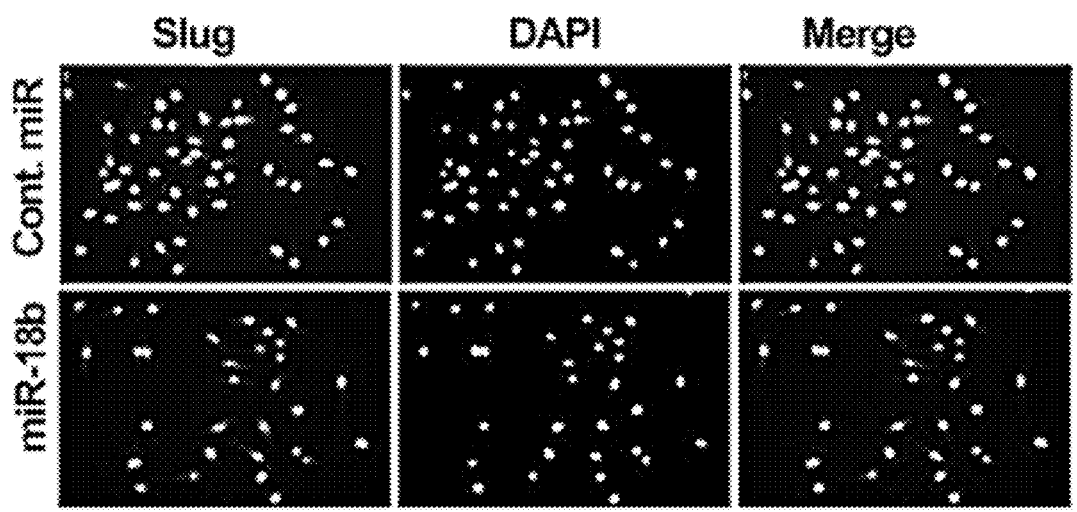
Figure 8E:
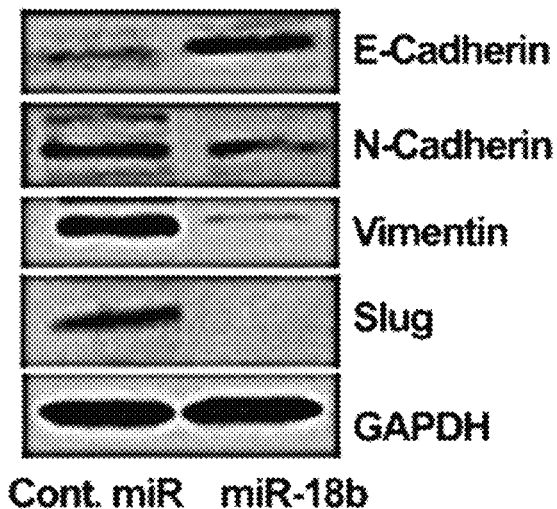

The effects of miR-18b on the migration and invasive behavior of 1205-Lu melanoma cells, a highly invasive cell type, were studied. miR-18b over-expression significantly suppressed the migratory ability and invasiveness of 1205-Lu melanoma cells (see FIG. 8A-B). The potential effects of miR-18b on EMT, given its role in the invasive and metastatic behavior of tumor cells, was then analyzed (Alonso et al., *Cancer Res* 67: 3450-60 (2007)). miR-18b overexpression in 1205-Lu melanoma cells resulted in significant upregulation of the epithelial biomarker E-cadherin (see FIG. 8E). By contrast, the levels of the mesenchymal markers vimentin, N-cadherin and slug were reduced in miR-18b overexpressing melanoma cells (see FIG. 8C-D-E). These findings suggest that loss of miR-18b expression enhances the migratory and invasive behavior of melanoma cell lines and promotes epithelial to mesenchymal transition.

Figure 9:
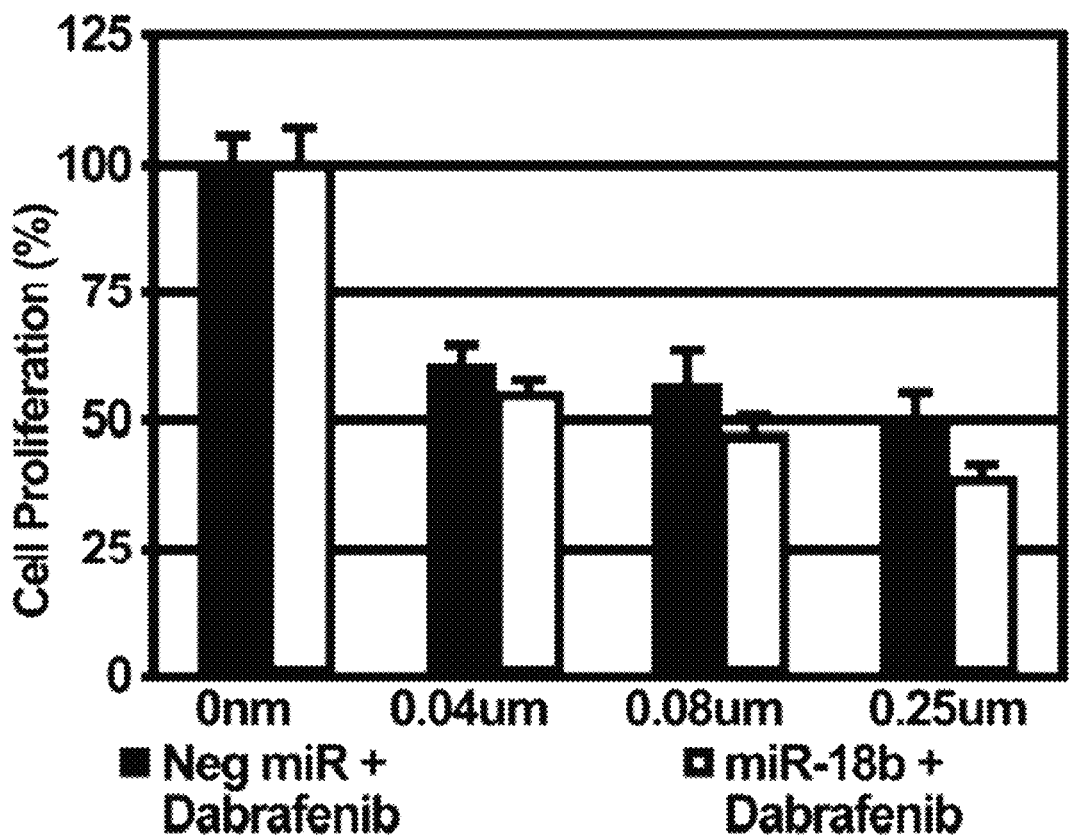
FIG. 9 shows the effect of miR-18b with BRAF inhibitor on cell proliferation of melanoma cell lines.

To determine whether combination therapy can provide additional benefits, 1205-Lu melanoma cells were transfected with Neg-miR (i.e., a random sequence as a negative control) or miR-18b and treated with dabrafenib and cell proliferation was observed after 48 hrs of treatment. Overexpression of miR-18b sensitized melanoma cell lines to BRAF specific inhibitor (see, e.g., FIG. 9). These observations indicate that miR-18b had an additive effect with BRAF inhibitor and its expression can be used as a parameter to assess the sensitivity to BRAF specific drugs in melanoma.

A number of embodiments have been described herein. Nevertheless, it will be understood that various modifications may be made without departing from the spirit and scope of this disclosure. Accordingly, other embodiments are within the scope of the following claims.

What is claimed is:

1. A method of detecting increased methylation of 2500 base pair (bp) region upstream of miR-18b in a human melanoma sample comprising: (i) obtaining a DNA sample from melanoma biopsy of the human subject; (ii) treating the DNA sample with bisulfite; (iii) measuring the methylation status of a 2500 bp region upstream of miR-18b in the subject's sample by using methylation specific primers in a methylation specific polymerase chain reaction, wherein the methylation specific primers consist of the sequence of SEQ ID NO:4 and 5; (iv) comparing the methylation status of the 2500 bp region in the subject's DNA sample with the mean methylation status of the 2500 bp region from two or more benign nevi samples; and (v) identifying whether the subject's DNA sample has increased methylation for the 2500 bp region in comparison to the mean methylation status for the 2500 bp region in the two or more benign nevi samples.

2. The method of claim 1, wherein the two or more benign nevi samples are from tissue biopsies.

3. The method of claim 2, wherein the two or more benign nevi samples comprise benign nevi samples from the subject.

* * * * *

SEQUENCE LISTING

<160> NUMBER OF SEQ ID NOS: 11

<210> SEQ ID NO 1
<211> LENGTH: 23
<212> TYPE: RNA
<213> ORGANISM: Homo sapiens

<400> SEQUENCE: 1
uaaggugcau cuagugcagu uag                                              23

<210> SEQ ID NO 2
<211> LENGTH: 71
<212> TYPE: RNA
<213> ORGANISM: Homo sapiens

<400> SEQUENCE: 2
uguguuaagg ugcaucuagu gcaguuagug aagcagcuua gaaucuacug cccuaaaugc      60
cccuucuggc a                                                          71

<210> SEQ ID NO 3
<211> LENGTH: 22
<212> TYPE: RNA
<213> ORGANISM: Homo sapiens

<400> SEQUENCE: 3
ugcccuaaau gccccuucug gc                                               22

<210> SEQ ID NO 4
<211> LENGTH: 18
<212> TYPE: DNA
<213> ORGANISM: Artificial Sequence
<220> FEATURE:
<223> OTHER INFORMATION: Oligonucleotide Primer MSP-F

<400> SEQUENCE: 4
gaggcgtggg tttggcgc                                                    18

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer MSP-R

<400> SEQUENCE: 5
caccacgcgc tccaatcctc                                                  20

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide primer USP-F

<400> SEQUENCE: 6 tcgttttaa ttggtttta ttagc                                              25

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide primer USP-R

<400> SEQUENCE: 7

```
tcaaaatttc ttaacaaata tcgtt                                        25

<210> SEQ ID NO 8
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 8
gcttgaatgg agaactccg                                               19

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 9
cttacctaat gctcccgttg a                                            21

<210> SEQ ID NO 10
<211> LENGTH: 25
<212> TYPE: DNA
<213> ORGANISM: Artificial Sequence
<220> FEATURE:
<223> OTHER INFORMATION: 3' UTR of MDM2 from homo sapiens

<400> SEQUENCE: 10
gctgggatta caggcatgca ccacc                                        25

<210> SEQ ID NO 11
<211> LENGTH: 26
<212> TYPE: DNA
<213> ORGANISM: Artificial Sequence
<220> FEATURE:
<223> OTHER INFORMATION: 3' UTR of MDM2 (mutated) from homo sapiens

<400> SEQUENCE: 11
gctgggatta caggcagcat gttacc                                       26
```